United States Patent [19]

Hadley et al.

[11] 4,350,691

[45] Sep. 21, 1982

[54] CERTAIN AZABICYCLOCARBOXAMIDES AND COMPOSITIONS CONTAINING SAME

[75] Inventors: Michael S. Hadley, Sawbridgeworth; Frank E. Blaney, London, both of England

[73] Assignee: Beecham Group Limited, England

[21] Appl. No.: 213,237

[22] Filed: Dec. 5, 1980

[30] Foreign Application Priority Data

Dec. 20, 1979 [GB] United Kingdom ............ 7943985

[51] Int. Cl.³ ............... C07D 451/04; C07D 451/14; A61K 31/46; A61K 31/33
[52] U.S. Cl. ..................................... 424/244; 424/265; 424/267; 424/274; 260/239 BF; 260/244.4; 260/245.7; 260/326.25; 546/112; 546/124; 546/125; 546/132
[58] Field of Search ............. 546/124, 112, 125, 132; 260/244.4, 245.7, 239 BF, 326.25; 424/244, 274, 265, 267

[56] References Cited

FOREIGN PATENT DOCUMENTS

| 13138 | 7/1980 | European Pat. Off. ............ 546/124 |
| 2748260 | 5/1978 | Fed. Rep. of Germany ...... 546/112 |
| 1259992 | 3/1961 | France ................................ 546/124 |
| 2042522 | 9/1980 | United Kingdom ................ 544/323 |

OTHER PUBLICATIONS

Roberts and Caserio, Basic Principles of Organic Chemistry, pp. 563-564.

Primary Examiner—Alan L. Rotman
Attorney, Agent, or Firm—Jacobs & Jacobs

[57] ABSTRACT

Compounds of the formula (III) and pharmaceutically acceptable salts thereof:

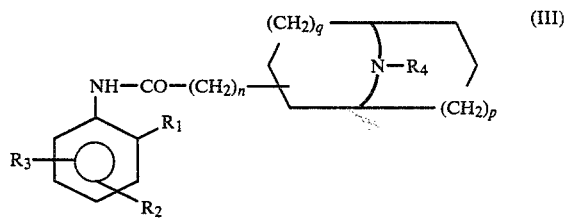

wherein:
$R_1$ is a $C_{1-6}$ alkoxy or $C_{1-6}$ alkylthio group;
$R_2$ and $R_3$ are the same or different and are hydrogen, halogen, $CF_3$, $C_{1-7}$acyl, $C_{1-7}$ acylamino or amino, aminocarbonyl or aminosulphonyl optionally substituted by one or two $C_{1-6}$ alkyl groups, $C_{1-6}$ alkylsulphonyl, $C_{1-6}$ alkylsulphinyl, $C_{1-6}$alkoxy, $C_{1-6}$ alkylthio, hydroxy or nitro or $R_1$ and $R_2$ taken together are methylenedioxy or ethylenedioxy in which case $R_3$ is any one of the groups given for $R_2$ and $R_3$ above;
$R_4$ is $C_{1-7}$ alkyl or a group $-(CH_2)_sR_6$ where s is 0 to 2 and $R_6$ is a $C_{3-8}$ cycloalkyl group, or a group $-(CH_2)_tR_7$ where t is 1 or 2 and $R_7$ is a phenyl group optionally substituted by one or two substituents selected from $C_{1-6}$ alkyl, $C_{1-4}$alkoxy, trifluoromethyl and halogen, or a thienyl group; and
n, p and q are independently 0 to 2 having useful pharmocological activity, a process for their preparation and their use.

17 Claims, No Drawings

CERTAIN AZABICYCLOCARBOXAMIDES AND COMPOSITIONS CONTAINING SAME

The present invention relates to novel aniline derivatives having pharmacological activity, to pharmaceutical compositions containing them, and to a process for their prepration.

Metoclopramide, which is of the formula (I):

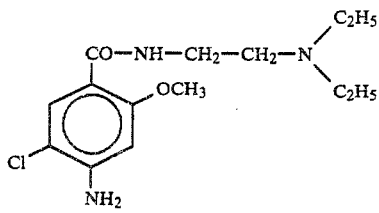

has found widespread clinical use owing to its ability to enhance the rate of gastric emptying.

A group of compounds of the formula (II):

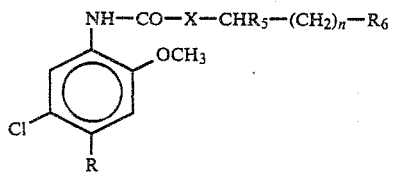

wherein X is a bridging group of the formula (a), (b), (c), or (d):

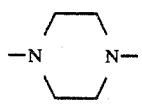 (a)

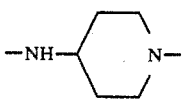 (b)

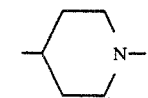 (c)

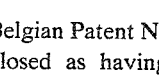 (d)

are disclosed in Belgian Patent No. 866,057. These compounds are disclosed as having major tranquillising activity.

A class of substituted aniline derivatives has now been found, the derivatives having a bicyclic side chain and thus being structurally distinct from the foregoing compounds; these derivatives have dopamine antagonist activity.

Accordingly the present invention provides compounds of the formula (III) and pharmaceutically acceptable salts thereof:

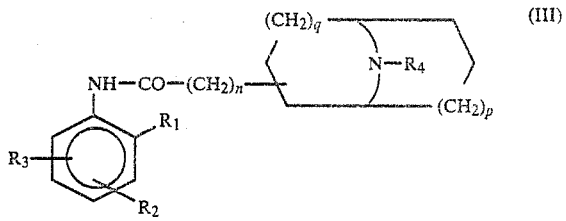

wherein:

$R_1$ is a $C_{1-6}$ alkoxy or $C_{1-6}$ alkylthio group;

$R_2$ and $R_3$ are the same or different and are hydrogen, halogen, $CF_3$, $C_{1-7}$ alkanoyl, $C_{1-7}$ alkanoylamino or amino, aminocarbonyl or aminosulphonyl optionally substituted by one or two $C_{1-6}$ alkyl groups, $C_{1-6}$ alkylsulphonyl, $C_{1-6}$ alkylsulphinyl, $C_{1-6}$alkoxy, $C_{1-6}$ alkylthio, hydroxy or nitro or $R_1$ and $R_2$ taken together are methylenedioxy or ethylenedioxy in which case $R_3$ is any one of the groups given for $R_2$ and $R_3$ above;

$R_4$ is $C_{1-7}$ alkyl or a group $—(CH_2)_sR_6$ where s is 0 to 2 and $R_6$ is a $C_{3-8}$ cycloalkyl group, or a group $—(CH_2)_tR_7$ where t is 1 or 2 and $R_7$ is a phenyl group optionally substituted by one or two substituents selected from $C_{1-6}$ alkyl, $C_{1-4}$ alkoxy, trifluoromethyl and halogen, or a thienyl group; and n, p and q are independently 0 to 2.

Suitable examples of the group $R_1$ include methoxy, ethoxy and n- and iso-propoxy, methylthio, ethylthio, and n- and iso-propylthio. Preferably $R_1$ is a methoxy group.

Suitable examples of the groups $R_2$ and $R_3$ include the following groups: hydrogen, chlorine, bromine, amino, $C_{1-4}$ alkanoylamino such as formylamino, acetylamino, propionylamino, n- and iso-butyrylamino, aminosulphonyl, and amino and aminosulphonyl substituted by one or two methyl, ethyl, n- or iso-propyl, n-, sec- or tert-butyl groups, nitro, methoxy, ethoxy, n- and iso-propoxy, methylthio, ethylthio, n- and iso-propylthio, and hydroxy.

Particularly suitable $R_2$ and $R_3$ groups include hydrogen, halogen, amino, methoxy and $C_{1-4}$ alkinoylamino as defined.

When $R_2$ and $R_3$ are other than $C_{1-6}$ alkoxy or $C_{1-6}$ alkylthio, it is generally preferred that $R_2$ is in the 4-position relative to the bicycloalkyl (alkyl) alkanoylamino side chain for greater activity in the resultant compound of the formula (III). For the same reason it is generally preferred that $R_3$ is in the 5-position relative to the same alkanoylamino side chain. When one of $R_2$ and $R_3$ is $C_{1-6}$ alkoxy, it is preferably methoxy and the other is hydrogen.

Particularly preferred $R_2$ groups include 4-amino and 4-(acylated amino), especially 4-acetylamino as defined. Preferably $R_2$ is 4-amino or 4-acetylamino. Particularly preferred $R_3$ groups include 5-halo, such as 5-chloro. Other $R_3$ groups of interest include substituted 5-aminosulphonyl as defined and 5-$C_{1-6}$ alkylsulphonyl or -sulphinyl, such as 5-aminosulphonyl and 5-methyl sulphonyl.

When $R_1$ and $R_2$ taken together are methylenedioxy or ethylenedioxy $R_1$ and $R_2$ are preferably ethylenedioxy.

Often the amide and heterocycle nitrogen atoms, which are in the same side chain, are separated by 3, 4 or 5 carbon atoms, preferably 4.

Suitable examples of R$_4$ when C$_{1-7}$ alkyl include methyl, ethyl, n- and iso- and n, sec- and tert-butyl. Within C$_{1-7}$ alkyl, C$_{5-7}$ alkyl are of interest and suitable examples thereof include n-pentyl, n-hexyl and n-heptyl and 3-methylbutyl.

When R$_4$ is a group —(CH$_2$)$_s$R$_6$ as defined, suitable examples of R$_6$ include C$_{5-8}$ cycloalkyl, preferably cyclohexyl. s is preferably 1.

When R$_4$ is a group —(CH$_2$)$_t$R$_7$ as defined, t is preferably 1.

When R$_7$ is optionally substituted phenyl as defined above, suitable examples of such optionally phenyl substituents include methyl, ethyl, n- and iso- propyl, n-, sec, and tert-butyl; methoxy, ethoxy, n- and iso-propoxy; CF$_3$, fluoro, chloro or bromo. One preferred R$_7$ when optionally substituted phenyl is unsubstituted.

When R$_7$ is thienyl it may be 2- or 3-thienyl, generally 2-thienyl.

R$_4$ is preferably benzyl, optionally substituted as hereinbefore defined, or 2-thienylmethyl, also called 2-thenyl. Optionally substituted benzyl is particularly preferred.

n is preferably 0. q is suitably 0 or 1, preferably 1.
p is suitably 0 or 1, preferably 0.

The pharmaceutically acceptable salts of the compound of the formula (III) include acid addition salts with conventional acids such as hydrochloric, hydrobromic, phosphoric, sulphuric, citric, tartaric, lactic and acetic acid.

The pharmaceutically acceptable salts of the compounds of the formula (III) also include quaternary ammonium salts. Examples of such salts include such compounds quaternised by compounds such as R$_8$-Y wherein R$_8$ is C$_{1-6}$ alkyl, phenyl-C$_{1-6}$ alkyl or C$_{5-7}$ cycloalkyl, and Y is a radical corresponding to an anion of an acid. Suitable examples of R$_8$ include methyl, ethyl and n- and iso-propyl; and benzyl and phenylethyl. Suitable examples of Y include the halides such as chloride, bromide and iodide.

Examples of pharmaceutically acceptable salts also include internal salts such as N-oxides.

The compounds of the formula (III) may also form hydrates and the invention extends to such hydrates.

A group of compounds within those of formula (III) consists of those wherein:

R$_1$ is C$_{1-6}$ alkoxy;

R$_2$ and R$_3$ are the same or different and are hydrogen, halogen, trifluoromethyl, C$_{2-7}$ alkanoylamino, C$_{1-7}$ alkanoylamino, or amino, aminocarbonyl or aminosulphonyl optionally substituted by one or two C$_{1-6}$ alkyl groups; C$_{1-6}$ alkylsulphonyl or nitro; or R$_1$ and R$_2$ taken together are methylenedioxy or ethylenedioxy, in which case R$_3$ may be any one of the groups given for R$_1$ and R$_2$ above;

R$_4$ is C$_{1-7}$ alkyl or a group —(CH$_2$)$_s$R$_6$ where s is 0 to 2 and R$_6$ is a C$_{3-8}$ cycloalkyl group, or a group —(CH$_2$)$_t$R$_7$ where t is 1 or 2 and R$_7$ is a phenyl group optionally substituted by one or two substituents selected from C$_{1-6}$ alkyl, C$_{1-6}$ alkoxy, trifluoromethyl and halogen; and n, p and q are independently 0 to 2.

From the aforesaid it will be seen that suitably the moiety of formula (IV):

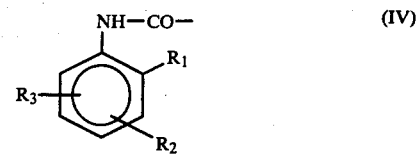

in a compound of the formula (III) will have the structure (V):

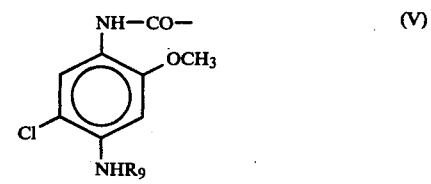

wherein R$_9$ is hydrogen or C$_{1-4}$ alkanoylamino.

A preferred group of compounds within those of formula (III), are those of formula (VI):

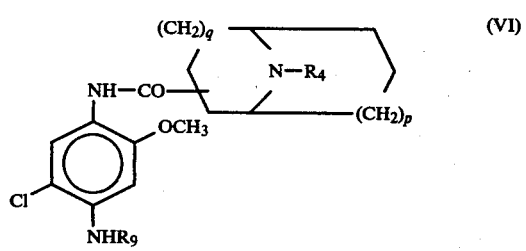

wherein R$_4$, R$_9$, p and q are as defined in formulae (III) and (V).

More suitably p is 0 or 1, it is believed preferably 0. Preferably q is 1 and the moiety of formula (IV) is then attached at the 3-position (standard numbering).

Suitable and preferred examples of R$_4$ in formula (VI) include those listed under formula (III) for R$_4$. Particularly preferred examples of R$_4$ include benzyl optionally substitued in the phenyl ring as defined under formula (III). Unsubstituted benzyl is an especially preferred R$_4$.

Preferably R$_9$ is hydrogen, formyl or acetyl.

A sub-group of compounds within those of formula (VI) are those of the formula (VII):

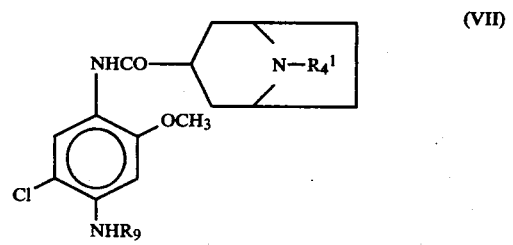

wherein R$^1_4$ is C$_{5-7}$ alkyl, and R$_9$ is as hereinbefore defined.

Suitable examples of R$^1_4$ are as so described for R$_4$ C$_{5-7}$ alkyl under formula (III). R$_9$ is preferably hydrogen, formyl or acetyl.

It is preferred that the NHCO moiety is in the β-orientation to the nortropane ring, that is as follows:

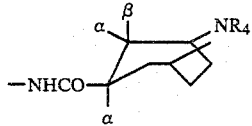

(The 2α and 2β orientations are also depicted.)

A particularly preferred sub-group of compounds within those of formula (VI) are those of the formula (VIII):

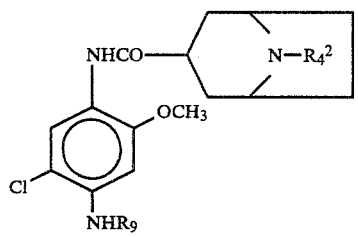

(VIII)

wherein $R^2_4$ is a group —$(CH_2)_tR^1_7$ wherein t is 1 or 2 and $R^1_7$ is optionally substituted phenyl as defined in formula (III); cyclohexylmethyl; or 2-thienylmethyl, and $R_9$ is as hereinbefore defined.

Suitable and preferred $R^2_4$ are as so described for the corresponding $R_4$ groups under formula (III).

$R^2_4$ benzyl is one especially preferred value.

It is preferred that the NHCO moiety is in the β-orientation to the nortropane ring.

A sub-group of compounds within those of the formula (VI) of interest are those of the formula (IX):

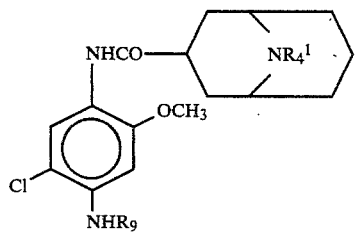

(IX)

wherein $R^1_4$ and $R_9$ are as defined in formula (VII).

Suitable and preferred $R^1_4$ and $R_9$ are as described under formula (VII).

It is preferred that the NHCO moiety is in the β-orientation to the granatane ring, the β-orientation being the same as in the nortropane hereinbefore depicted.

Another sub-group of compounds within those of the formula (VI) of interest are those of the formula (X):

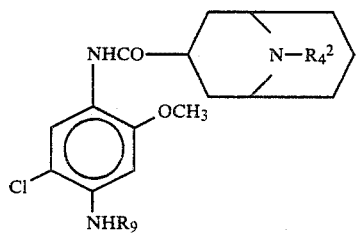

(X)

wherein $R^2_4$ and $R_9$ are as defined in formula (VIII).

Suitable and preferred examples of $R^2_4$ and $R_9$ are as described under formula (VIII).

It is preferred that the NHCO moiety is in the β-orientation to the granatane ring.

A second group of compounds within those of the formula (III) which is of interest is of the formula (XI):

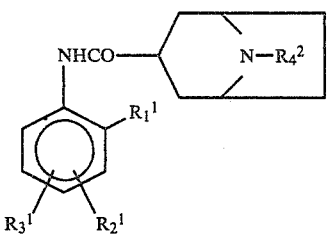

(XI)

wherein:

$R^1_1$ is $C_{1-6}$ alkoxy;

$R^1_2$ and $R^1_3$ are the same or different and are hydrogen, aminosulphonyl optionally substituted by one or two $C_{1-6}$ alkyl groups, $C_{1-6}$ alkylsulphonyl, $C_{1-6}$ alkylsulphinyl, $C_{1-6}$ alkoxy or hydroxy or $R^1_1$ and $R^1_2$ taken together are methylenedioxy or ethylenedioxy, in which case $R^1_3$ is any one of the groups given above for $R^1_2$ and $R^1_2$; and $R^2_4$ is as defined in formula (VIII).

It is preferred that the NHCO moiety is in the β-orientation to the nortropane ring.

More suitably $R^1_1$ is methoxy, or together with $R^1_2$ is ethylenedioxy.

One of $R^1_2$ and $R^1_3$ is preferably hydrogen, and the other and $R^1_1$ are then preferably both methoxy.

Suitable and preferred $R^2_4$ are as so described under formula (VIII).

A sub-group of compounds within those of formula (XI) are those of the formula (XII):

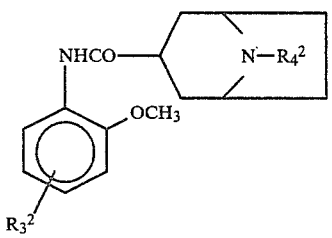

(XII)

wherein $R^2_3$ is aminosulphonyl optionally substituted by one or two $C_{1-6}$ alkyl groups or $C_{1-6}$ alkylsulphonyl or $C_{1-6}$ alkylsulphinyl and $R^2_4$ as hereinbefore defined.

$R^2_3$ is preferably aminosulphonyl or methylsulphonyl, in particular 5-aminosulphonyl or 5-methylsulphonyl (with respect to the carboxamido side chain taken as 1).

Suitable and preferred $R^2_4$ are as so described under formula (VIII).

A second sub-group of compounds within those of formula (XI) are those of the formula (XIII):

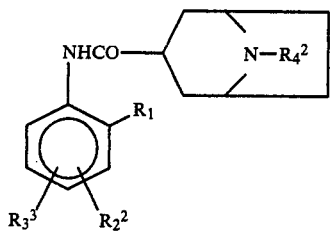

wherein:

$R^1_1$ and $R^2_4$ are defined in formula (XI);

$R^2_2$ and $R^3_3$ are the same or different and are $C_{1-6}$ alkoxy or hydrogen; or $R^1_1$ and $R^2_2$ taken together are methylenedioxy or ethylenedioxy, in which case $R^3_3$ is any one of the groups given above for $R^2_2$ and $R^3_3$.

Suitable and preferred $R^1_1$, $R^2_2$, $R^3_3$ and $R^2_4$ are so described under formula (XI).

In particular $R^1_1$, and $R^2_2$ or $R^3_3$ when $C_{1-6}$ alkoxy, are preferably both methoxy.

From the aforesaid it will also be seen that a third group of compounds within formula (III) of interest are those of the formula (XIV):

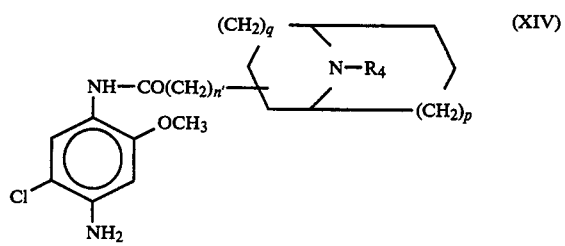

wherein n' is 1 or 2 and the remaining variables are as defined in formula (III).

More suitably p and q independently are 0 or 1; preferably p is 0 and q is 1. Preferably n is 1.

Suitable and preferred examples of $R_4$ include those listed hereinbefore for $R_4$.

A fourth group of compounds within formula (III) of interest are those of the formula (XV):

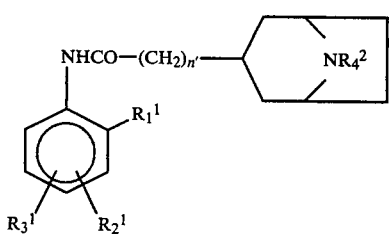

wherein:

n' is 1 or 2 and $R^1_1$, $R^1_2$, $R^1_3$ and $R^2_4$ are as defined in formula (XI).

Preferably n is 1.

Suitable and preferred $R^1_1$, $R^1_2$, $R^1_3$ and $R^2_4$ are as so described under formula (XI).

Particularly suitable examples of the compounds of the present invention include those of the Examples hereinafter. These are:

4-chloro-2-(8'-benzyl-8'-azabicyclo[3.2.1]octane-3'β-carboxamido)anisole, 5-nitro-4-chloro-2-(8'-benzyl-8'-azabicyclo[3.2.1]octane-3'β-carboxamido)anisole, 5-amino-4-chloro-2-(8'-benzyl-8'-azabicylo[3.2.1]octane-3'β-carboxamido)anisole, 5-acetamido-4-chloro-2-(8'-benzyl-8'-azabicyclo[3.2.1]octane-3'β-carboxamido)anisole, 5-formamido-4-chloro-2-(8'-benzyl-8'-azabicylo[3.2.1]octane-3'β-carboxamido)anisole, 4-chloro-2-(8'-[4''-chlorobenzyl]-8'-azabicyclo(3.2.1]octane-3'β-carboxamido)anisole 5-nitro-4-chloro-2-(8'-[4''-chlorobenzyl]-8'-azabicyclo[3.2.1]octane-3'β-carboxamido)anisole, 5-amino-4-chloro-2-(8'-[4''-chlorobenzyl]-8'-azabicyclo[3.2.1]octane-3'β-carboxamido)anisole, 5-acetamido-4-chloro-2-(8'-[4''-chlorobenzyl]-8'-azabicyclo[3.2.1]octane-3'β-carboxamido)anisole, 5-formamido-4-chloro-2-(8'-[4''-chlorobenzyl]-8'-azabicyclo[3.2.1]octane-3'β-carboxamido)anisole, 4-chloro-2-(8'-[4''-methylbenzyl]-8'-azabicyclo[3.2.1]octane-3'β-carboxamido)anisole, 5-nitro-4-chloro-2-(8'-[4''-methylbenzyl]-8'-azabicyclo[3.2.1]octane-3'β-carboxamido)anisole, 5-amino-4-chloro-2-(8'-[4''-methylbenzyl]-8'-azabicyclo[3.2.1]octane-3'β-carboxamido)anisole, 5-acetamido-4-chloro-2-(8'-(4''-methylbenzyl]-8'-azabicyclo[3.2.1]octane-3'β-carboxamido)anisole, 5-formamido-4-chloro-2-(8'-[4''methylbenzyl]-8'-azabicyclo[3.2.1]octane-3'β-carboxamido)anisole, 4-chloro-2-(8'-[4''-methoxybenzyl]-8'-azabicyclo[3.2.1]octane-3'β-carboxamido)anisole, 5-nitro-4-chloro-2-(8'-[4''-methoxybenzyl]-8'-azabicyclo[3.2.1]octane-3'β-carboxamido)anisole, 5-amino-4-chloro-2-(8'-[4''-methoxybenzyl]-8'-azabicyclo[3.2.1]octane-3'β-carboxamido)anisole, 5-acetamido-4-chloro-2-(8'-[4''-methoxybenzyl]-8'-azabicyclo[3.2.1]octane-3'β-carboxamido)anisole, 5-formamido-4-chloro-2-(8'-[4''-methoxybenzyl]-8'-azabicyclo[3.2.1]octane-3'β-carboxamido)anisole, 4-chloro-2-(8'-[3'',4''-dichlorobenzyl]-8'-azabicyclo[3.2.1]octane-3'β-carboxamido)anisole, 5-nitro-4-chloro-2-(8'-[3'',4''-dichlorobenzyl]-8'-azabicyclo[3.2.1]octane-3'β-carboxamido)anisole, 5-amino-4-chloro-2-(8'-[3'',4''-dichlorobenzyl]-8'-azabicyclo[3.2.1]octane-3'β-carboxamido)anisole, 5-acetamido-4-chloro-2-(8'-[3'',4''-dichlorobenzyl]-8'-azabicyclo[3.2.1]octane-3'β-carboxamido)anisole, 5-formamido-4-chloro-2-(8'-[3'',4''-dichlorobenzyl]-8'-azabicyclo[3.2.1]-octane-3'β-carboxamido)anisole, 4-chloro-2-(8'-[3''-trifluoromethylbenzyl]-8'-azabicyclo[3.2.1]octane-3'β-carboxamido)anisole, 5-nitro-4-chloro-2-(8'-[3''-trifluoromethylbenzyl]-8'-azabicyclo[3.2.1]octane-3'β-carboxamido)anisole, 5-amino-4-chloro-2-(8'-[3''-trifluoromethylbenzyl]-8'-azabicyclo[3.2.1]octane-3'β-carboxamido)anisole, 5-acetamido-4-chloro-2-(8'-[3''-trifluoromethylbenzyl]-8'-azabicyclo[3.2.1]octane-3'β-carboxamido)anisole, 5-formamido-4-chloro-2-(8'-[3''-trifluoromethylbenzyl]-8'-azabicyclo[3.2.1]octane-3'β-carboxamido)anisole, 4-chloro-2-(8'-β-phenethyl)-8'-azabicyclo[3.2.1]octane-3'β-carboxamido)anisole, 5-nitro-4-chloro-2-(8'-β-phenethyl)-8'-azabicyclo[3.2.1]octane-3'β-carboxamido)anisole, 5-amino-4-chloro-2-(8'-β-phenethyl)-8'-azabicyclo[3.2.1]octane-3'β-carboxamido)anisole, 5-acetamido-4-chloro-2-(8'-β-phenethyl)-8'-azabicyclo[3.2.1]octane-3'β-carboxamido)anisole, 5-formamido-4-chloro-2-(8'-β-phenethyl)-8'-azabicyclo[3.2.1]-octane-3'β-carboxamido)anisole, 4-chloro-2-(8'-[2-thenyl]-8'-azabicyclo[3.2.1]octane-3'β-carboxamido)anisole,
5-nitro-4-chloro-2-(8'-[2-thenyl]-8'-azabicyclo[3.2.1]octane-3'β-carboxamido)anisole,
5-amino-4-chloro-2-(8'-[2-thenyl]-8'-azabicyclo[3.2.1]octane-3'β-carboxamido)anisole,
5-acetamido-4-chloro-2-(8'-[2-thenyl]-8'-azabicyclo[3.2.1]octane-3'β-carboxamido)anisole,
5-formamido-4-chloro-2-(8'-[2-thenyl]-8'-azabicyclo[3.2.1]octane-3'β-carboxamido)anisole,
4-chloro-2-(8'-hexyl-8'-azabicyclo[3.2.1]octane-3'β-carboxamido)anisole,
5-nitro-4-chloro-2-(8'-hexyl-8'-azabicyclo[3.2.1]octane-3'β-carboxamido)anisole,
5-amino-4-chloro-2-(8'-hexyl-8'-azabicyclo[3.2.1]octane-3'β-carboxamido)anisole,
5-acetamido-4-chloro-2-(8'-hexyl-8'-azabicyclo[3.2.1]octane-3'β-carboxamido)anisole,
5-formamido-4-chloro-2-(8'-hexyl-8'-azabicyclo[3.2.1]octane-3'β-carboxamido)anisole,
4-chloro-2-(8'-[3''-methylbutyl]-8'-azabicyclo[3.2.1]octane-3'β-carboxamido)anisole,
5-nitro-4-chloro-2-(8'-[3''-methylbutyl]-8'-azabicyclo[3.2.1]octane-3'β-carboxamido)anisole,
5-amino-4-chloro-2-(8'-[3''-methylbutyl]-8'-azabicyclo[3.2.1]octane-3'β-carboxamido)anisole,
5-acetamido-4-chloro-2-(8'-[3''-methylbutyl]-8'-azabicyclo[3.2.1]octane-3'β-carboxamido)anisole,
5-formamido-4-chloro-2-(8'-[3''-methylbutyl]-8'-azabicyclo[3.2.1]octane-3'β-carboxamido)anisole,
4-chloro-2-(8'-cyclohexyl-8'-azabicyclo[3.2.1]octane-3'β-carboxamido)anisole,
5-nitro-4-chloro-2-(8'-cyclohexyl-8'-azabicyclo[3.2.1]octane-3'β-carboxamido)anisole,
5-amino-4-chloro-2-(8'-cyclohexyl-8'-azabicyclo[3.2.1]octane-3'β-carboxamido)anisole,
5-acetamido-4-chloro-2-(8'-cyclohexyl-8'-azabicyclo[3.2.1]octane-3'β-carboxamido)anisole,
5-formamido-4-chloro-2-(8'-cyclohexyl-8'-azabicyclo[3.2.1]-octane-3'β-carboxamido)anisole,
4-chloro-2-(8'-cyclohexylmethyl-8'-azabicyclo[3.2.1]octane-3'β-carboxamido)anisole,
5-nitro-4-chloro-2-(8'-cyclohexylmethyl-8'-azabicyclo[3.2.1]octane-3'β-carboxamido)anisole,
5-amino-4-chloro-2-(8'-cyclohexylmethyl-8'-azabicyclo[3.2.1]octane-3'β-carboxamido)anisole,
5-acetamido-4-chloro-2-(8'-cyclohexylmethyl-8'-azabicyclo[3.2.1]octane-3'β-carboxamido)anisole,
5-formamido-4-chloro-2-(8'-cyclohexylmethyl-8'-azabicyclo[3.2.1]octane-3'β-carboxamido)anisole,
4-aminosulphonyl-2-(8'-benzyl-8-azabicyclo[3.2.1]octane 3'β-carboxamido)anisole,
4-methylsulphonyl-2-(8'-benzyl-8-azabicyclo[3.2.1]octane-3'β-carboxamido)anisole,
2-methoxy-3-(8'-benzyl-8'-azabicyclo[3.2.1]octane-3'β-carboxamido)anisole,
3-methoxy-2-(8'-benzyl-8'-azabicyclo[3.2.1]octane-3'β-carboxamido)anisole,
3-methoxy-4-(8'-benzyl-8'-azabicyclo[3.2.1]octane-3'β-carboxamido)anisole,
4-methoxy-2-(8'-benzyl-8'-azabicyclo[3.2.1]octane-3'β-carboxamido)anisole,
2,3-ethylenedioxy-(8'-benzyl-8'-azabicyclo[3.2.1]octane-3'β-carboxanilide,
4-chloro-2-(8'-benzyl-8'-azabicyclo[3.2.1]heptane-2'-(+)-α-carboxamido)anisole,
5-nitro-4-chloro-2-(8'-benzyl-8'-azabicyclo[3.2.1]heptane-2'-(+)-α-carboxamido)anisole,
5-amino-4-chloro-2-(8'-benzyl-8'-azabicyclo[3.2.1]heptane-2'-(+)-α-carboxamido)anisole,
5-acetamido-4-chloro-2-(8'-benzyl-8'azabicyclo[3.2.1]heptane-2'(+)-α-carboxamido)anisole,
5-formamido-4-chloro-2-(8'-benzyl-8'-azabicyclo[3.2.1]heptane-2'-(+)-α-carboxamido)anisole,
4-chloro-2-(8'-benzyl-8'-azabicyclo[3.2.1]heptane-2'-(−)-α-carboxamido)anisole,
5-nitro-4-chloro-2-(8'-benzyl-8'-azabicyclo[3.2.1]heptane-2'-(−)-α-carboxamido)anisole,
5-amino-4-chloro-2-(8'-benzyl-8'-azabicyclo[3.2.1]heptane-2'-(−)-α-carboxamido)anisole,
5-acetamido-4-chloro-2-(8'-benzyl-8'-azabicyclo[3.2.1]heptane-2'-(−)-α-carboxamido)anisole,
5-formamido-4-chloro-2-(8'-benzyl-8'-azabicyclo[3.2.1]heptane-2'-(−)-α-carboxamido)anisole,
4-chloro-2-(8'-benzyl-8'-azabicyclo[3.2.1]octane-2'(+)-α-acetamido)anisole,
5-nitro-4-chloro-2-(8'-benzyl-8'-azabicyclo[3.2.1]octane-2'-(+)-α-acetamido)anisole,
5-amino-4-chloro-2-(8'-benzyl-8'-azabicyclo[3.2.1]octane-2'-(+)-α-acetamido)anisole,
5-acetamido-4-chloro-2-(8'-benzyl-8'-azabicyclo[3.2.1]octane-2'-(+)-α-acetamido)anisole,
5-formamido-4-chloro-2-(8'-benzyl-8'-azabicyclo[3.2.1]octane-2'-(+)-α-acetamido)anisole,
4-chloro-2-(8'-benzyl-8'-azabicyclo[3.2.1]octane-2'-(−)-α-acetamido)anisole,
5-nitro-4-chloro-2-(8'-benzyl-8'-azabicyclo[3.2.1]octane-2'-(−)-α-acetamido)anisole,
5-amino-4-chloro-2-(8'-benzyl-8'-azabicyclo[3.2.1]octane-2'-(−)-α-acetamido)anisole,
5-acetamido-4-chloro-2-(8'-benzyl-8'-azabicyclo[3.2.1]octane-2'-(−)-α-acetamido)anisole,
5-formamido-4-chloro-2-(8'-benzyl-8'-azabicyclo[3.2.1]octane-2'-(−)-α-acetamido)anisole,
4-chloro-3-(8'-benzyl-8'-azabicyclo[3.2.1]octane-3'-β-acetamido)anisole,
5-nitro-4-chloro-3-(8'-benzyl-8'-azabicyclo[3.2.1]octane-3'-β-acetamido)anisole,
5-amino-4-chloro-3-(8'-benzyl-8'-azabicyclo[3.2.1]octane-3'-β-acetamido)anisole,
5-acetamido-4-chloro-3-(8'-benzyl-8'-azabicyclo[3.2.1]octane-3'-β-acetamido)anisole,
5-formamido-4-chloro-3-(8'-benzyl-8'-azabicyclo[3.2.1]octane-3'-β-acetamido)anisole,
4-chloro-2-(8'-benzyl-8'-azabicyclo[3.2.1]octane-3'-α-acetamido)anisole,
5-nitro-4-chloro-2-(8'-benzyl-8'-azabicyclo[3.2.1]octane-3'-α-acetamido)anisole,
5-amino-4-chloro-2-(8'-benzyl-8'-azabicyclo[3.2.1]octane-3'-α-acetamido)anisole,
5-acetamido-4-chloro-2-(8'-benzyl-8'-azabicyclo[3.2.1]octane-3'-α-acetamido)anisole,
5-formamido-4-chloro-2-(8'-benzyl-8'-azabicyclo[3.2.1]octane-3'-α-acetamido)anisole, It will of course be realised that the compounds of the formula (III) have chiral or prochiral centres, and thus are capable of existing in a number of stereoisomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The invention also provides a process for the preparation of a compound of formula (III) or a pharamaceutically acceptable salt thereof which process comprises reacting an acid of formula (XVI):

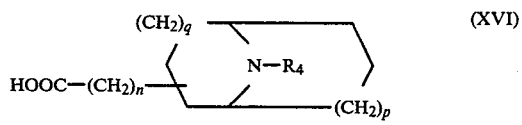

wherein the remaining variables are as defined in formula (III) or a reactive derivative thereof with a compound of formula (XVII):

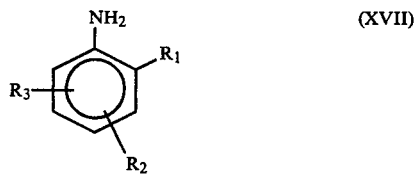

wherein the variables are as defined in formula (III); with the proviso that $R_2$ or $R_3$ is not amino; and thereafter if desired or necessary converting a group $R_2$ or $R_3$ in the thus formed compound to another group $R_2$ or $R_3$ respectively; converting $R_4$ to another $R_4$; and optionally forming a pharmaceutically acceptable salt of the resultant compound of the formula (III).

"Reactive derivative" when used herein means a derivative of the acid (XVI) which can be reacted with the compound (XVII) to form an amido linkage between the acid group of the compound (XVI) and the amino group of the compound.

Often this reactive derivative will be formed in situ, for instance by reacting the acid (XVI) and the compound (XVII) in the present of a dehydrating catalyst such as a carbodiimide, for example dicyclohexylcarbodiimide. This is a preferred process method. The acid (XIV) is preferably in the form of an acid addition salt, such as a hydrohalide, in particular the hydrochloride.

These reactions may be carried out at any nonextreme temperature such as $-10°-100°$ C. and more suitably $0°-80°$ C. The higher reaction temperatures are employed with less active acids of the formula (XVI) whereas the lower temperatures are employed with the more reactive acids of the formula (XVII).

The reaction will normally be carried out in a nonhydroxylic solvent, inert to both reactants such as benzene, toluene, diethyl ether, tetrahydrofuran, dichloromethane or N,N-dimethylformamide.

The "reactive derivative" may also be the acid halide. The reaction will then normally be carried out in an inert, non-hydroxylic solvent such as those listed hereinbefore preferably in the presence of an acid acceptor. The acid acceptor is suitably an organic base such as a tertiary amine eg triethylamine, trimethylamine, pyridine or picoline or an inorganic acid acceptor, such as calcium carbonate, sodium carbonate, potassium carbonate or the like. It should also be noted that it is possible to use certain acid acceptors as the inert solvent, for example organic bases.

The reaction may also be carried out by forming an anhydride of the acid (XVI) in the usual manner, and reacting that with the compound (XVII). Normally a conventional mixed anhydride will be used, such as one formed from ethyl chloroformate.

These reaction may be carried out under the same conditions as reaction in the presence of a dehydrating agent.

The intermediates of the formula (XVI) and (XVII) are either known compounds or can be prepared by analogous processes to known compounds.

The skilled man will appreciate that the choice or necessity of conversion of groups $R_2$ and/or $R_3$ to other groups $R_2$ and/or $R_3$ will be dictated by the nature and position of substituents $R_1$, $R_2$ and $R_3$.

It will be apparent that compounds of the formula (III) containing an $R_2$, $R_3$ or $R_4$ group which is convertible to another $R_2$, $R_3$ or $R_4$ group are useful intermediates, and as such form an important aspect of the invention.

By way of example of such conversions, the compounds of the formula (III) wherein $R_2$ or $R_3$ is a nitro group may be prepared via the nitration of the corresponding intermediate product wherein $R_2$ or $R_3$ is a hydrogen atom.

A particularly suitable nitrating agent for use in this process is fuming nitric acid in the presence of sulphuric acid. In general the reagent is added to a solution of the intermediate wherein $R_2$ or $R_3$ is hydrogen, in solution in an organic solvent such as acetic acid. Normally the reaction is carried out at or below ambient temperature, for example $0°-30°$ C. and more suitably at about $5°-20°$ C., subject to the reaction medium remaining fluid.

The nitro compound may be obtained from the reaction mixture by such conventional means as neutralisation followed by extraction into a water immiscible organic solvent such as ethyl acetate or dichloromethane from which it may be recovered by evaporation. If desired the nitro compound may be purified by chromatography or by recrystallisation of the free base or an acid addition salt thereof.

An optional process step provided by this invention in the preparation of the compounds of the formula (III) wherein $R_2$ or $R_3$ is an amino group comprises the reduction of a corresponding intermediate wherein $R_2$ or $R_3$ is a nitro group.

The reduction of the intermediates wherein $R_2$ or $R_3$ is a nitro group may be effected with reagents known to be suitable for reducing nitroanisole to aminoanisole. A suitable reagent for this reduction is stannous chloride in hydrochloric acid or in mixtures of hydrochloric and acetic acid. The desired amino compound may be obtained from the reaction mixture by respectively neutralisation followed by extraction into a water immiscible solvent such as ethyl acetate from which it may be receoved by evaporation of the solvent.

Another suitable method is catalytic hydrogenation at atmospheric pressure in polar solvent such as ethanol. Transition metal catalysts such as Raney nickel are often used. The desired compound may be obtained from the reaction mixture by filtration and evaporation to dryness.

The initial crude product in both cases may be purified by chromatography or crystallisation or by forming an acid addition salt which may be recrystallised.

Those compounds of the invention wherein $R_2$ or $R_3$ is a $C_{1-7}$ acylamino group may be prepared from the corresponding intermediate wherein $R_2$ or $R_3$ is an amino group by reaction with an acylating derivative of the corresponding acid. Suitable acylating derivatives are as previously described as suitable acylating derivatives of the acid of the formula (XVI). The reaction may proceed as described for the reaction of the compounds of the formula (XVI) and (XVII). For an $R_2/R_3$ formamido group acylation may be effected with the free acid.

This invention also provides an optional process for the preparation of a compound of the formula (III) wherein $R_2$ or $R_3$ is an amino group which process comprises the deacylation of a corresponding intermediate wherein $R_2$ or $R_3$ is a $C_{1-7}$ acylamino group.

Generally the hydrolysis reaction may be effected by treatment with a base such as an alkali metal hydroxide.

Also a compound of the formula (III) wherein $R_2$ or $R_3$ is halogen may be prepared by a conventional halogenation of the corresponding intermediate wherein the said $R_2$ or $R_3$ is hydrogen.

Similarly the compounds wherein $R_2$ or $R_3$ is $C_{1-6}$ alkylthio or $C_{1-6}$ alkylsulphinyl may be oxidised to the corresponding compounds wherein $R_2$ or $R_3$ is $C_{1-6}$ alkylsulphinyl or $C_{1-6}$alkylsulphonyl respectively.

These oxidations may conveniently be carried out conventionally at below ambient temperatures using an organic peracid in a non-aqueous inert reaction medium preferably a chlorinated hydrocarbon solvent, for example using 3-chloroperbenzoic acid, or using a water soluble inorganic strong oxidant, such as an alkali metal permanganate or hydrogen peroxide in aqueous solution.

It will be appreciated by the skilled man that, depending on the other specific substituents in the compound of the formula (III), such an oxidation on a compound of the formula (III) may also form the N-oxide of the bicyclic moiety therein.

Given the specific substitution desired and having been decided whether the compound or its N-oxide is required, the skilled man will readily ascertain whether such $R_2/R_3$ interconversion is desirable.

It will be appreciated that, when $R_4$ in the compound of the formula (III) is $R_5$, which is optionally substituted benzyl as hereinbefore defined; $R_4$ may be replaced by another group $R_4$.

Such $R_5$ benzyl groups may be removed for example by conventional transition metal catalysed hydrogenolysis to give a compound of the formula (XVIII):

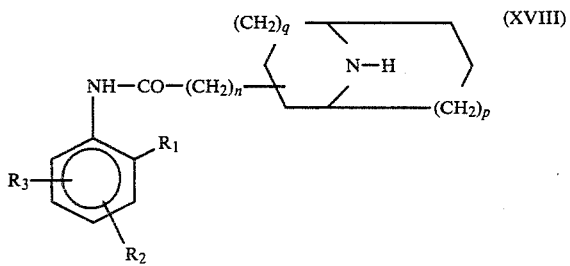

wherein $R_1$, $R_2$ and $R_3$ as defined in formula (III).

This invention also provides a further process for an optional process step in the preparation of a compound of the formula (III) which comprises the reaction of a corresponding compound of the formula (XVIII) as hereinbefore defined with a compound $QR_4$ wherein $R_4$ is as defined in formula (III) and Q is a group or atom readily displaced by a nucleophile.

Suitable values for Q include Cl, Br, I, $OSO_2CH_3$ or $OSO_2C_6H_4pCH_3$.

Favoured values for Q include Cl, Br and I.

$R_4$ will suitably be other than optionally substituted benzyl as hereinbefore defined, but it will be apparent that this process step will be apt for $R_4$ benzyl when substituted by substituents which may be deleteriously affected by any subsequent reactions.

The reaction may be carried out under conventional alkylation conditions, for example in an inert solvent such as dimethylformamide in the presence of an acid acceptor such as potassium carbonate. Generally the reaction is carried out at a non-extreme temperature such as at ambient or at a slightly elevated temperature.

It will be appreciated that, when $R_2$, $R_3$ or $R_4$ are converted to other $R_2$, $R_3$ or $R_4$, then these conversions may take place in any desired or necessary order.

Since the compounds of the formula (III) are nitrogenous bases they are able to form acid addition salts in a conventional manner. Most suitably these salts are those formed with pharmaceutically acceptable inorganic and organic acids such as hydrochloric, hydrobromic, orthophosphoric, methanesulphuric, toluenesulphonic, acetic, fumaric, tartaric, lactic, citric or succinic acid. Those compounds of the invention which contain more than one basic nitrogen atom may form di-acid addition salts as well as mono-acid addition salts, for example the dihydrochloride salt as well as the monohydrochloride salt.

The acid addition salts of compounds of the formula (III) may be prepared in entirely conventional manner by reacting a compound of the formula (III) with the chosen acid.

The quaternary ammonium salts of the compounds of the formula (III) may be prepared in conventional manner for such salts, such as by reaction of the chosen compound of the formula (III) with a compound $R_8Y$ as hereinbefore defined. This reaction is suitably carried out in an appropriate solvent such as acetone, methanol, ethanol, dimethylformamide and the like, at ambient or raised temperature and pressure.

The N-oxides of the compounds of the formula (III) may be prepared in conventional manner, as hereinbefore described.

The synthesis of a compound of the formula (III) is illustrated by the following Scheme:

Scheme

-continued
Scheme

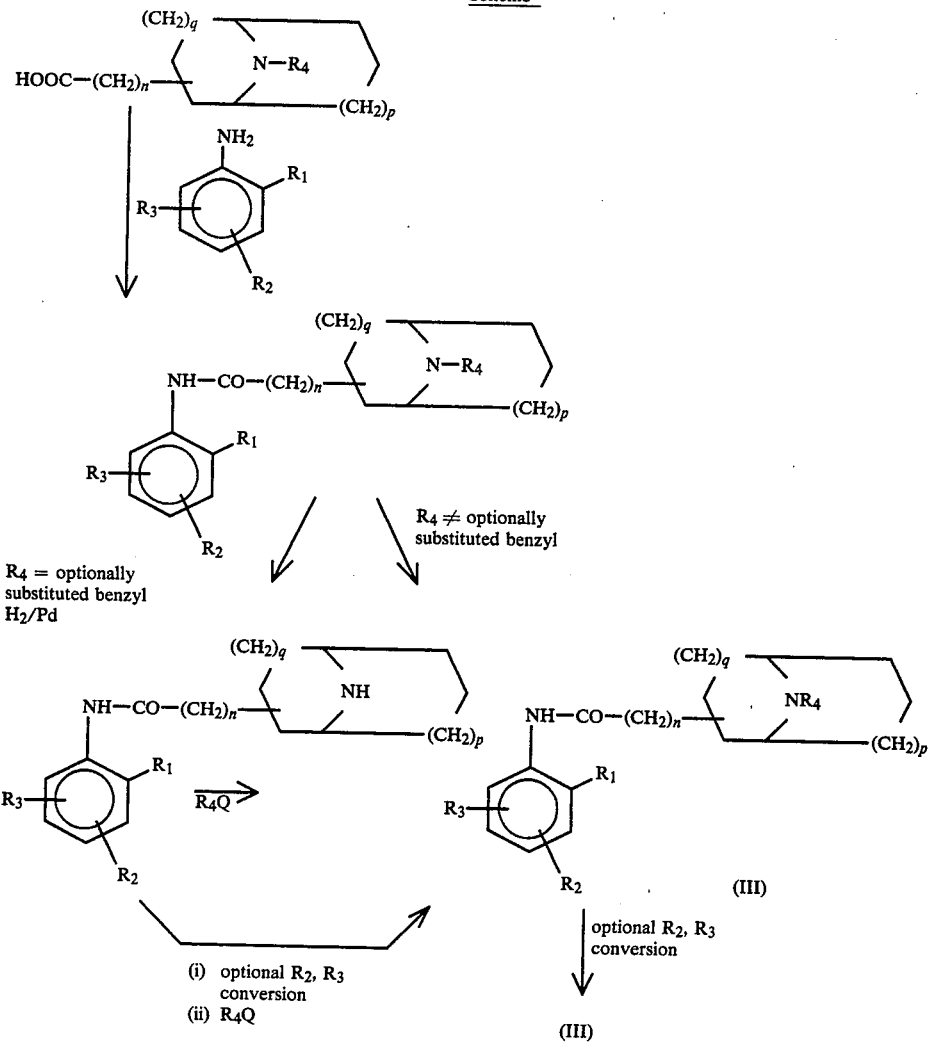

It will be realised that in the compound of the formula (III) the —NHCO—(CH$_2$)$_n$— linkage may have an α or β orientation with respect to the ring of the bicyclic moiety to which it is attached. A mixture of α and β isomers of the compound of the formula (III) may be synthesised non-stereospecifically and the desired isomer separated conventionally therefrom eg by chromatography; or alternatively the α and β isomer may if desired be synthesised from the corresponding α or β form of the compound of the formula (XVI).

Synthesis from the corresponding α or β isomer of the compound of the formula (XVI) is in general preferred.

It will be appreciated that, when n=0 in the compounds of the formulae (III) or (XVI) epimerisation of the CO-ring linkage to the energetically more favourable orientation often takes place readily in the presence of acid or base. In such cases if the less favoured isomer is desired, it is preferred to stereospecifically synthesise the isomer of the compound of the formula (XVI) and to convert it to the required compound of the formula (III) under such conditions to avoid epimerisation.

The α or β form of the compound of the formula (XVI) may if desired be prepared by known stereospecific processes, such as those leading to the α or β isomers of the compound of the formula (XVI) depicted in the Schemes and described in the Descriptions hereinafter.

The precursor of the compound of the formula (XVI) may be stereospecifically synthesised, such as the of Description and then converted to the corresponding desired isomer of the compound of the formula (XVI) under non-stereospecific conditions with retention of configuration. Alternatively, the precursor may itself have no chiral or prochiral centre at the relevant position, such as that of Description 5. but be converted under stereospecific conditions to the desired isomer of the compound of the formula (XVI).

Alternatively, a mixture of the α and β isomers of the compound of the formula (XVI) may be synthesised nonstereospecifically and the desired isomer separated conventionally therefrom eg by chromatography. However, in this case it is generally more convenient to react the mixture to give a mixture of α and β isomers of the compound of the formula (III) and to separate these if desired as hereinbefore described.

The ketones and αβ-unsaturated carboxylic acids which are the starting materials, depicted in Schemes 1 and 2, for the intermediates of the formula (XVI), are known compounds or may be prepared by analogy with known compounds.

The following Scheme 1 illustrates preparative routes to intermediates of the formula (XVI) wherein n is 0.

Additionally, intermediates wherein p is 1 may be more conveniently prepared by conversion of the ketone >CO group to a >CH.CHO group by the method of Corey et al., Tet. Letters, 1980, 21, 3539, and oxidising this to the corresponding acid function.

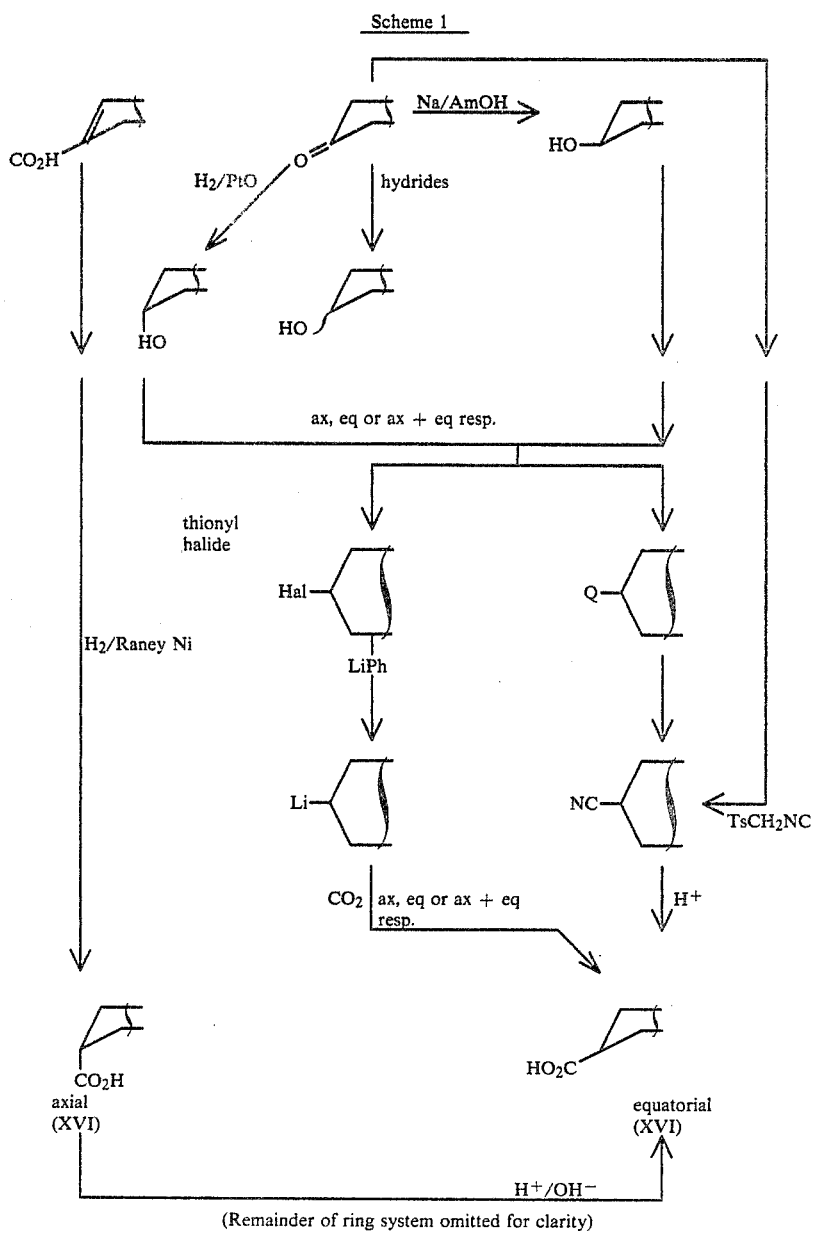

(Remainder of ring system omitted for clarity)

The following Scheme 2 illustrates preparative routes to intermediates of the formula (XVI) wherein n is 1 or 2.

Scheme 2

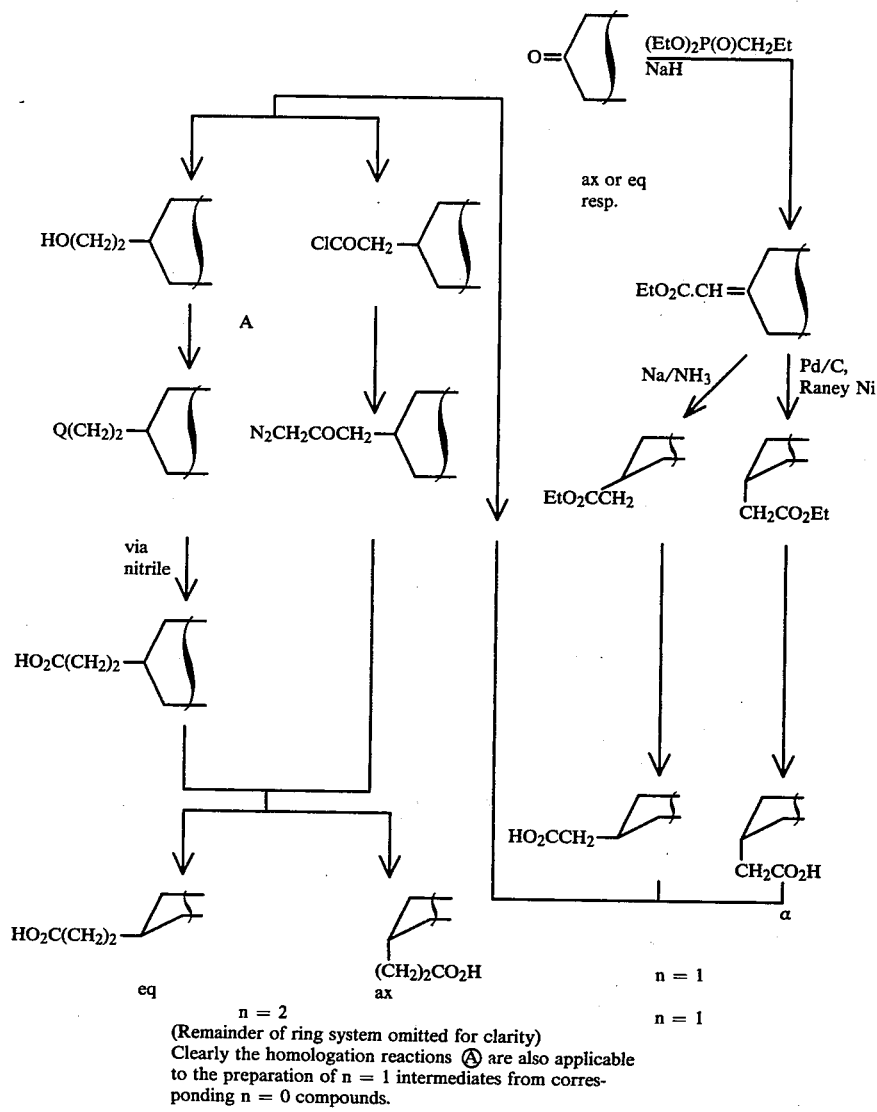

(Remainder of ring system omitted for clarity)
Clearly the homologation reactions Ⓐ are also applicable to the preparation of n = 1 intermediates from corresponding n = 0 compounds.

As hereinbefore stated, the compounds of the formula (III) are dopamine antagonists.

Depending on their balance between central and peripheral action, the compounds of the formula (III) may be used in the treatment of disorders of the central nervous system, such as psychosis, and/or in the treatment of disorders related to impaired gastro-intestinal motility, such as retarded gastric emptying, dyspepsia, flatulence, oesophagal reflux peptic ulcer, and emesis.

All the compounds of the formula (III) may be used in the treatment of emesis.

Examples of compounds of the formula (III) which are of particular interest for their CNS activity, in particular anti-pyschotic activity, are those wherein $R_4$ is $R_4{}^2$, in particular optionally substituted benzyl as hereinbefore defined, especially compounds of formula (VIII).

Examples of compounds of the formula (III) which are of interest for their anti-emetic activity and for their beneficial effect on gastric motility are those wherein the anilide benzene nucleus bears an optionally mono- or di-alkylated aminosulphonyl or an alkylsulphonyl or alkylsulphinyl substituent and $R_4$ is $R_4{}^2$, in particular optionally substituted benzyl, as hereinbefore defined, and especially compounds of formula (XII). Examples of compounds of interest for their beneficial effect on gastric motility are the quaternary ammonium salts of the compounds of the formula (III).

The invention therefore also provides a pharmaceutical composition comprising a compound of the formula (III) or a pharmaceutically acceptable salt thereof, together with a pharmaceutically acceptable carrier. Such compositions may be adapted for oral or parental administration, and as such may be in the form of tablets, capsules, syrups, reconstitutable powders, injectable and infusable solutions or suspensions and the like; the compositions may also be in the form of suppositories and the like. Normally orally administrable compositions are preferred.

The invention further provides a method of treatment of maladies in humans comprising the administration of an effective amount of a compound of the formula (III) or a pharmaceutically acceptable salt thereof. The "effective amount" will depend in the usual way on a number of factors such as the nature and severity of the malady to be treated, and the actual compound used. The compositions of this invention will most suitably be presented as unit dose compositions containing from 1 to 100 mg, more usually from 2.5 to 50 mg, for example from 5 to 25 mg, such as 7.5, 10.0, 12.5 or 15 mg. Such compositions will normally be taken from 1 to 6 times daily, for example 3 or 4 times daily so that the total amount of active agent administered is within the range 2.5 to 200 mg.

Preferred unit dosage forms include tablets and capsules.

The compositions of this invention may be formulated by conventional methods of blending, filling and compressing.

Suitable carriers for use in this invention include diluents, binders, disintegrants, colouring agents, flavouring agents and preservatives. These agents may be utilized in conventional manner, for example in a manner similar to that already used for other mood modifying agents.

The following Examples illustrate the preparation of the compounds of formula (III) and the following Descriptions illustrate the preparation of the intermediates thereto.

Description 1

8-Benzyl-8-azabicyclo-[3.2.1]-octane-3β-nitrile (D1)

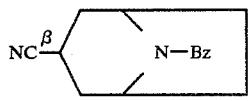

8-Benzylnortropan-3-one (6.81 g, 31.6 mmol) was dissolved in dimethoxyethane (200 ml) containing tosyl methyl isocyanide (11.06 g, 56.6 mmol). The solution was cooled in an ice bath and ethanol (4.5 ml) was added followed by portionwise addition of potassium tert-butoxide (12.39 g, 110 mmol). The mixture was then heated at 50° C. for 5 hours, cooled and poured into a saturated salt solution (800 ml). This was extracted with ethyl acetate (3×50 ml) and the combined organic extracts were dried (Na₂SO₄) filtered and evaporated to give a black tarry mixture (9.5 g), containing the product. This was chromatographed on silica gel. Elution with 30% ethyl acetate/petrol gave the desired nitrile (4.97 g, 70%) which was contaminated with a little starting ketone.

The following are prepared analogously:
8-(4'-chlorobenzyl-8-azabicyclo[3.2.1]-octane-3β-nitrile (D2);
8-(4'-methylbenzyl)-8-azabicyclo[3.2.1]-octane-3β-nitrile (D3);
8-(4'-methoxybenzyl)-8-azabicyclo[3.2.1]octane-3β-nitrile (D4);
8-(3',4'-dichlorobenzyl)-8-azabicyclo[3.2.1]octane-3β-nitrile (D5)
8-(3'-trifluoromethylbenzyl)-8-azabicyclo[3.2.1]octane-3β-nitrile (D6);
8-β-phenethyl-8-azabicyclo-[3.2.1]octane-3β-nitrile (D7);
8-(2'-thenyl)-8-azabicyclo[3.2.1]octane-3β-nitrile (D8);
8-hexyl-8-azabicyclo[3.2.1]octane-3β-nitrile (D9);
8-(3'-methylbutyl)-8-azabicyclo[3.2.1]octane-3β-nitrile (D10);
8-cyclohexylmethyl-8-azabicyclo[3.2.1]octane-3β-nitrile (D11).

Description 2

8-Benzyl-azabicyclo[3.2.1]octane-3β-carboxylic acid (D12)

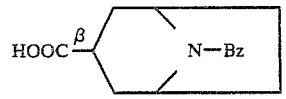

The crude nitrile (4.97 g) from the previous reaction was dissolved in dry methanol (60 ml) in a 3-necked round-bottomed flask fitted with a gas-inlet tube and reflux condenser. Hydrogen chloride gas was bubbled through the solution for a period of 3 hours during which time the solution started to reflux. The mixture was allowed to sit overnight at room temperature. Most of the methanol was evaporated and the remaining oil was dissolved in water. This was neutralised with saturated potassium carbonate solution and extracted with ether (3×200 ml). The combined ether extracts were dried (Na₂SO₄), filtered and evaporated to yield a brown oil (4.56 g) containing the ester.

This was vigorously stirred with distilled water (100 ml) and the mixture heated under reflux for 24 hours. The mixture was then cooled and extracted with ethyl acetate (2×125 ml). The aqueous layer was evaporated to dryness yielding the desired nortropane acid as a white solid (3.65 g, 88%), m.p. 216°-223° C. Evaporation of the ethyl acetate extracts gave a brown oil (0.8 g) identified as the starting ketone.

The following are prepared analogously:
8-(4'-chlorobenzyl)-8-azabicyclo[3.2.1]octane-3β-carboxylic acid (D13) (58%);
8-(4'-methylbenzyl)-8-azabicyclo[3.2.1]octane-3β-carboxylic acid (D14) (54%);
8-(4'-methoxybenzyl)-8-azabicyclo[3.2.1]octane-3β-carboxylic acid (D15);
8-(3',4'-dichlorobenzyl)-8-azabicyclo[3.2.1]octane-3β-carboxylic acid (D16);
8-(3'-trifluoromethyl)-8-azabicyclo[3.2.1]octane-3β-carboxylic acid (D17);
8-β-phenethyl-8-azabicyclo[3.2.1]octane-3β-carboxylic acid (D18);
8-(2'-thenyl)-8-azabicyclo[3.2.1]-octane-3β-carboxylic acid (D19);
8-hexyl-8-azabicyclo[3.2.1]octane-3β-carboxylic acid (D20);
8-(3'-methylbutyl)-8-azabicyclo[3.2.1]octane-3β-carboxylic acid (D21);
8-cyclohexylmethyl-8-azabicyclo[3.2.1]octane-3β-carboxylic acid (D22).

Description 3

8-Cyclohexyl-8-azabicyclo[3.2.1]octane-3β-carboxylic acid (D23)

Methyl 8-azabicyclo[3.2.1]octane-3β-carboxylate (1.53 g) and cyclohexanone (0.98 g) were dissolved in benzene (175 ml) containing para-toluenesulphonic acid (0.2 g). This was heated at reflux for 48 hours during which time the water was azeotropically removed via a Dean-Stark system. The solution was then evaporated to dryness and the oil was dissolved in 200 ml of tetrahydrofuran:methanol (3:1). The pH of the mixture was adjusted to 3.5 using ethanolic hydrogen chloride and sodium cyanoborohydride (0.8 g) was added. The pH was maintained throughout the reaction at ca 5 by occasional addition of ethanolic hydrogen chloride. After stirring the mixture overnight, the solvents were removed in vacuo, the mixture basified with potassium carbonate solution and extracted with dichloromethane (4×150 ml). Drying (Na$_2$SO$_4$) and removal of solvent gave the product as a pale yellow oil (1.8 g; 82%). This was quantitatively converted to 8-cyclohexyl-8-azabicyclo(3.2.1)octane-3β-carboxylic acid by heating the ester at reflux with distilled water for 36 hours and subsequently evaporating the aqueous solution to dryness.

Description 4

Methyl 8-benzyl-8-azabicyclo(3.2.1)octan-3-one-2-carboxylate (D24)

This was prepared following the procedure described by S P Findlay, J Org Chem (1957) 22, 1385, substituting benzylamine hydrochloride for methylamine hydrochloride. Following this procedure methyl 8-benzyl-8-azabicyclo(3.2.1)octan-3-one-2-carboxylate was obtained as a yellow oil after purification by chromatography on silica gel. (47%)

Description 5

Methyl 8-benzyl-8-azabicyclo(3.2.1)oct-2-ene-2-carboxylate (D25)

The compound obtained from the previous description (1.05 g) was dissolved in methanol (80 ml) cooled in an ice bath. To this was added sodium borohydride (1 g) and the residue was allowed to stir overnight at room temperature. Removal of solvent gave a solid which was dissolved in 10% sodium carbonate solution and extracted with ethyl acetate (3×150 ml). This was dried and evaporated to yield an oil which was dissolved in 50 mls of 10% hydrochloric acid and heated at reflux for 4 hours. Evaporation of this solution gave the crude hydroxy acid as its hydrochloride salt. This was dissolved in phosphorous oxychloride (15 ml) and heated at reflux for 1 hour. All the solvents were removed in vacuo and the black oil was poured into methanol containing a molar excess of triethylamine. The mixture was allowed to stir overnight, then the solvents removed and the residues dissolved in 10% sodium carbonate solution and extracted with dichloromethane (3×150 ml). Purification by chromatography (silica gel) afforded methyl-8-benzyl-8-azabicyclo[3.2.1]oct-2-ene-2-carboxylate as a yellow oil (0.37 g; 37%).

Description 6

8-Benzyl-8-azabicyclo[3.2.1]octane-2-(+)-α-carboxylic acid (D26) and
8-benzyl-8-azabicyclo[3.2.1]octane-2-(−)-α-carboxylic acid (D27)

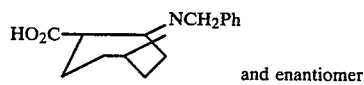

and enantiomer

The compound from the previous description (3.1 g) was dissolved in 400 ml ethanol and this was hydrogenated over Raney nickel at 60 psi for 24 hours. Removal of the catalyst by filtration and evaporation of solvent gave the mixture as a yellow oil, the proton magnetic resonance spectrum of which indicated partial loss of the benzyl moiety. The oil was, therefore, dissolved in dimethylformamide and benzyl chloride (1 g), and potassium carbonate (2 g) were added. This was allowed to stir over night, filtered and evaporated to yield the crude product as an oil. Purification of this by chromotography on silica gel gave methyl-8-benzyl-8-azabicyclo[3.2.1]octane-2-carboxylate (2.1 g) as an epimeric mixture. This was dissolved in dry methanol and treated with sodium amyloxide (1 g) at reflux over night. Removal of solvent, extraction from aqueous solution (ethyl acetate) and refluxing over night in distilled water followed by evaporation of the aqueous solution to dryness gave a racemic mixture of (D26) and (D27).

Description 7

8-Benzyl-8-azabicyclo[3.2.1]octane-2-(+)-α-acetic acid (D28) and
8-benzyl-8-azabicyclo[3.2.1]octane-2-(−)-α-acetic acid (D29)

and enantiomer

The compound of description 6 (1.3 g) as its hydrochloride salt was treated with thionyl chloride (2 g) in 25 ml of chloroform. This was heated at reflux for 3 hours, then the solvents were removed under reduced pressure and the crude acid chloride was washed twice with dry toluene (removing each time by evaporation under reduced pressure). This was dissolved in dry dichloromethane and added dropwise to a cooled (−10°) ethanol free ether solution of diazomethane. This was kept at −10° for several hours before allowing it to warm to room temperature. Removal of solvent under reduced pressure gave the crude diazoketone as an orange oil. This was not purified further but dissolved directly in ethanol and freshly prepared silver oxide (from 0.5 g silver nitrate) was added. This was heated at 50°-60° until the nitrogen evolution had ceased. The solution was allowed to cool, filtered and evaporated to give a brown oil, which after purification by chromatography on silica gel gave ethyl-8-benzyl-8-azabicyclo(3.2.1)-octane-2α-acetate. Refluxing this ester in 10% hydrochloric acid over night followed by evaporation gave 8-benzyl-8-azabicyclo(3.2.1)octane-2α-acetic acid as its hydrochloride salt, a racemate of the (+) form (D47) and (−) form (D48). 8-benzyl-8-aza-bicylco[3.2.1]octane-3β-acetic acid (D30) is similarly prepared from (D12) as its hydrochloride, (D50).

Description 8

3-carbethoxy methylene-8-benzyl-8-azabicyclo[3.2.1]octane (D31)

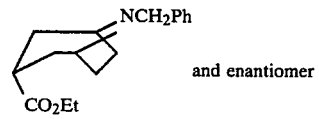

and enantiomer

A solution of triethylphosphonoacetate (3.91 g) in 20 ml dry toluene was syringed into a stirred mixture of 80% sodium and hydride (0.52 g) in toluene (30 ml) maintained under nitrogen. When reaction has subsided the solution was stirred for a further hour, then 2.5 g of 8-benzyl-8-azabicyclo(3.2.1)octan-3-one in dry toluene (40 ml) was added. The mixture was heated at reflux over night, then cooled, poured into water and extracted with chloroform. This was dried and evaporated. Purification by chromatography on silica gel gave 3-carbethoxy methylene-8-benzyl-8-azabicyclo(3.2.1)octane as a pale yellow oil (2.7 g, 81%).

Description 9

8-Benzyl-8-azabicyclo[3.2.1]-octane-3α-acetic acid (D32)

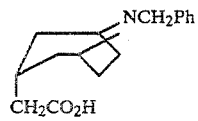

The compound of Description 8 (2.5 g) was hydrogenated for 60 hours in ethanol over Raney nickel at 60 psi. Filtration and removal of solvent gave a yellow oil which was dissolved in 50 ml of dimethylformamide containing benzyl chloride (1 g) and potassium carbonate (2 g). This was stirred over night, then the mixture was filtered and the solvent evaporated to a brown oil. Purification by chromatography on silica gel gave ethyl 8-benzyl-8-azabicyclo[3.2.1]octane-3α-acetate as a yellow oil. This was converted to 8-benzyl-8-azabicyclo[3.2.1]octane-3α-acetic acid as its hydrochloride salt (D49) by heating at reflux over night in dilute hydrochloric acid.

Description 10

8-Benzyl-8-azabicyclo[3.2.1]-3β-carboxylic acid hydrochloride (D33)

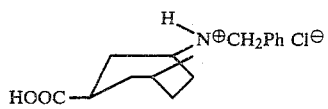

Excess dilute hydrochloric acid was added to 8-benzyl-8-azabicyclo[3.2.1]octane-3β-carboxylic acid. The mixture was evaporated under reduced pressure, toluene was added and the toluene removed under reduced pressure to dryness. The remaining solid was then dried in vacuo to give (D33) used without further purification.

Similarly prepared are:
8-(4′-chlorobenzyl)-8-azabicyclo[3.2.1]octane-3β-carboxylic acid hydrochloride (D34);
8-(3′,4′-dichlorobenzyl)-8-azabicyclo[3.2.1]octane-3β-carboxylic acid hydrochloride; (D35)
8-(4′-methylbenzyl)-8-azabicyclo[3.2.1]octane-3β-carboxylic acid hydrochloride (D36);
8-(4′-methoxybenzyl-8-(azabicyclo[3.2.1]octane-3β-carboxylic acid hydrochloride (D37);
8-(3′-trifluoromethylbenzyl)-8-azabicyclo[3.2.1]octane-3β-carboxylic acid hydrochloride (D38);
8-β-phenethyl-8-azabicyclo[3.2.1]octane-3β-carboxylic acid hydrochloride (D39);
2-thenyl-8-azabicyclo[3.2.1]octane-3β-carboxylic acid hydrochloride (D40);
8-hexyl-8-azabicyclo[3.2.1]octane-3β-carboxylic acid hydrochloride (D41);
8-(3′-methylbutyl)-8-azabicyclo[3.2.1]octane-3β-carboxylic acid hydrochloride (D42);
8-cyclohexyl-8-azabicyclo[3.2.1]octane-3β-carboxylic acid hydrochloride (D43)
8-cyclohexylmethyl-8-azabicyclo[3.2.1]octane-3β-carboxylic acid hydrochloride (D44);
8-benzyl-8-azabicyclo[3.2.1]octane-2-(+)-α-carboxylic acid hydrochloride (D45); and
8-benzyl-8-azabicyclo[3.2.1]octane-2-(−)-α-carboxylic acid hydrochloride (D46) as a racemate;
8-benzyl-8-azabicyclo[3.2.1]octane-2-(+)-α-acetic acid hydrochloride (D47); and
8-benzyl-8-azabicyclo[3.2.1]octane-2-(−)-α-acetic acid hydrochloride (D48) as a racemate;
8-benzyl-8-azabicyclo[3.2.1]octane-3α-acetic acid hydrochloride (D49);
8-benzyl-8-azabicyclo[3.2.1]-3β-acetic acid hydrochloride (D50);

Description 11

8-(3′,4′-Dichlorobenzyl)-8-azabicyclo[3.2.1]octane-3β-carboxylic acid hydrochloride (D35)

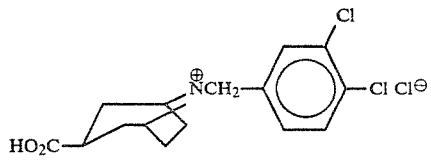

Methyl 3β-nortropane carboxylate (1.69 g) and 3,4-dichlorobenzyl chloride (1.96 g) in dimethyl formamide (50 ml) were stirred at room temperature for 48 hours in the presence of anhydrous potassium carbonate (1.38 g). Solvent was removed by evaporation and the residue dissolved in water and ethyl acetate. The ethyl acetate layer was separated, dried over potassium carbonate and evaporated to give an oil which was adsorbed on alumina (grade II). Elution with progressively graded mixtures of light petroleum, ether and ethyl acetate gave methyl 8-(3,4-dichlorobenzyl)-8-azabicyclo(3.2.1)-3β-carboxylate (2.95 g; 90%) as an oil.

This oil was suspended in water (200 ml) and heated at reflux with stirring overnight. Water was removed by evaporation under reduced pressure and excess dilute hydrochloric acid added. The mixture was evaporated under reduced pressure, toluene added and again evaporated. The remaining solid was then dried under vacuum to give 8-(3,4-dichlorobenzyl)-8-azabicyclo(3.2.1)-3β-carboxylic acid hydrochloride used without further purification.

Similarly prepared are:
8-benzyl-8-azabicyclo[3.2.1]octane-3β-carboxylic acid hydrochloride (D33);
8-(4′-chlorobenzyl)-8-azabicyclo[3.2.1]octane-3β-carboxylic acid hydrochloride (D34);
8-(4′-methylbenzyl)-8-azabicyclo[3.2.1]octane-3β-carboxylic acid hydrochloride (D36);
8-(4′-methoxybenzyl-8-(azabicyclo[3.2.1]octane-3β-carboxylic acid hydrochloride (D37);
8-(3′-trifluoromethylbenzyl)-8-azabicyclo[3.2.1]octane-3β-carboxylic acid hydrochloride (D38);
8-β-phenethyl-8-azabicyclo[3.2.1]octane-3β-carboxylic acid hydrochloride (D39);
2-thenyl-8-azabicyclo[3.2.1]octane-3β-carboxylic acid hydrochloride (D40);
8-hexyl-8-azabicyclo[3.2.1]octane-3β-carboxylic acid hydrochloride (D41);

8-(3′-methylbutyl)-8-azabicyclo[3.2.1]octane-3β-carboxylic acid hydrochloride (D42);

8-cyclohexylmethyl-8-azabicyclo[3.2.1]octane-3β-carboxylic acid hydrochloride (D44);

8-benzyl-8-azabicyclo[3.2.1]octane-2-(+)-α-carboxylic acid hydrochloride (D45); and 8-benzyl-8-azabicyclo[3.2.1]octane-2-(−)-α-carboxylic acid hydrochloride (D46) as a racemate;

8-benzyl-8-azabicyclo[3.2.1]octane-2-(+)-α-acetic acid hydrochloride (D47); and 8-benzyl-8-azabicyclo[3.2.1]octane-2-(−)-α-acetic acid hydrochloride (D48) as a racemate;

8-benzyl-8-azabicyclo[3.2.1]octane-3α-acetic acid hydrochloride (D49);

8-benzyl-8-azabicyclo[3.2.1]-3β-acetic acid hydrochloride (D50);

EXAMPLE 1a

4-Chloro-2-(8′-benzyl-8′-azabicyclo-[3.2.1]-octane-3′β-carboxamido)-anisole (1)

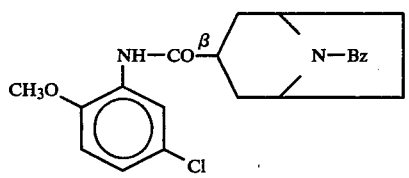

Exo-8-benzyl-8-azabicyclo-(3,2,1)-octan-3-carboxylic acid (3.14 g, 12.8 mmol) was stirred under reflux in 100 ml tetrahydrofuran with 2-amino-4-chloroanisole (2.22 g, 14 mmol) and dicyclohexylcarbodiimide (3.17 g) for 24 hours. This was cooled and filtered and the residue was washed with ethyl acetate. The combined organic extracts were evaporated to dryness and the resulting mixture was chromatographed on silica gel. Elution with ether gave the pure 4-chloro-2-[8′-benzyl-8′-azabicyclo-(3,2,1)-octane-3′-carboxamido]-anisole (2.0 g, 40%).

EXAMPLE 1b

4-Chloro-2-[8′-(3,4-dichlorobenzyl)-8′-azabicyclo-(3.2.1)-octane-3′β-carboxamido]anisole (2)

8-(3′,4′-Dichlorobenzyl)-8-azabicyclo(3.2.1)-octan-3′β-carboxylic acid hydrochloride (5.7 g), 2-amino-4-chloro-anisole (2.6 g) and dicyclohexylcarbodiimide (3.8 g) were stirred together in dimethyl formamide (100 ml) overnight at room temperature. Solvent was removed by evaporation under reduced pressure and dilute sodium hydroxide and ethyl acetate added. The mixture was filtered to removed dicyclohexyl urea and the ethyl acetate layer then separated, dried and evaporated. The residue was chromatographed on silica gel eluting with progressively graded mixtures of light petroleum, ether and ethyl acetate to give 4-chloro-2-[8′(3,4-dichlorobenzyl)-8′-azabicyclo(3.2.1)-octane-3β-carboxamido]-anisole. (5 g; 68%).

The following are prepared analogously:

4-chloro-2-(8′-[4″-chlorobenzyl]-8′-azabicyclo(3.2.1)octane-3α-carboxamido)anisole (3) from (D.34) (74% yield)

4-chloro-2-(8′-[4″-methylbenzyl]-8′-azabicyclo(3.2.1)octane-3α-carboxamido)anisole (4) from (D.36) (78% yield)

4-chloro-2-(8′-[4″-methoxybenzyl]-8′-azabicyclo(3.2.1)octane-3α-carboxamido)anisole (5) from (D.37) (74% yield)

4-chloro-2-(8′[3″-trifluoromethylbenzyl]-8′-azabicyclo[3.2.1)octane-3α-carboxamido)anisole (6) from (D.38)

4-chloro-2-(8′-β-phenethyl-8′-azabicyclo(3.2.1)octane-3α-carboxamido)anisole (7) from (D.39)

4-chloro-2-(8′-[2″-thenyl]-8′-azabicyclo(3.2.1)octane-3α-carboxamido)anisole (8) from (D.40)

4-chloro-2-(8′-hexyl-8′-azabicyclo(3.2.1)octane-3α-carboxamido)anisole (9) from (D.41) (85% yield)

4-chloro-2-(8′-(3″-methylbutyl)-8′-azabicyclo(3.2.1)octane-3α-carboxamido)anisole (10) from (D.42) (79% yield)

4-chloro-2-(8′-cyclohexyl-8′-azabicyclo(3.2.1)octane-3α-carboxamido)anisole (11) from (D.43) (52% yield)

4-chloro-2-(8′-cyclohexylmethyl-8′-azabicyclo(3.2.1)octane-3α-carboxamido)anisole (12) from (D.44) (75% yield)

4-chloro-2-(8′-benzyl-8′-azabicyclo[3.2.1]octane-2′-(+)-α-carboxamido)anisole (13) from (D.45), and 4-chloro-2-(8′-benzyl-8′-azabicyclo[3.2.1]octane-2′-(−)-α-carboxamido)anisole (14) from (D.46) as a racemate.

4-chloro-2-(8′-benzyl-8′-azabicyclo[3.2.1]octane-2′-(+)-α-acetamido)anisole (15) from (D.47), and 4-chloro-2-(8′-benzyl-8′-azabicyclo[3.2.1]octane-2′-(−)-α-acetamido)anisole (16) from (D.48), as a racemate.

4-chloro-2-(8′-benzyl-8′-azabicyclo[3.2.1]octane-3′α-acetamido)anisole (17) from (D.49), 4-chloro-2-(8′-benzyl-8′-azabicyclo[3.2.1]octane-3′β-acetamido)anisole (18) from (D.50).

2,3-ethylenedioxy-8′-benzyl-8′azabicyclo[3.2.1]octane-3′β-carboxanilide (19) from 2,3-ethylenedioxyaniline, (73% yield) mp 134°–5° C.;

4-chloro-2-(8′-benzyl-8′-azabicyclo[3.2.1]-octane-3′β-carboxamido)anisole (1) from (D33).

EXAMPLE 1c 3-methoxy-4-[8′-benzyl-8′-azabicyclo[3.2.1]octane-3β′-carboxamido]anisole (20)

2,4-dimethoxy aniline (1.19 g, 0.0078 moles), 8-benzyl-8-azabicyclo[3.2.1]octane-3β-carboxylic acid hydrochloride (2.2 g, 0.0078 moles) and dicyclohexyl carbodiimide (1.89 g, 0.0093 moles) in dry dimethylformamide (30 ml) were stirred together at room temperature over night. The solvent was removed under reduced pressure, 10% sodium hydroxide added and the aqueous solution extracted with ethyl acetate (3×50 ml). The combined organic extracts were washed with dilute hydrochloric acid, the aqueous washings basified with 10% sodium hydroxide solution and extracted with ethyl acetate (3×50 ml). The combined organic extracts were dried (MgSO₄) and removal of solvent gave a dark coloured oil. Column chromatography on silica gel eluting with ether gave 3-methoxy-4-[8-benzyl-8-azabicyclo(3.2.1)octane-3β-carboxamido]anisole (1.33 g, 45%), mp. 91°–2°.

The same procedure is used to prepare the following:

4-methoxy-2-(8′-benzyl-8′-azabicyclo[3.2.1]octane-3β-carboxamido)anisole (21) from 2,5-dimethoxyaniline (27% yield, mp. 119°14′ C.), 3-methoxy-2-(8′-benzyl-8′-azabicyclo[3.2.1]octane-3β-carboxamido)anisole (22) from 2,6-dimethoxyaniline, 2-methoxy-3-(8′-benzyl-8′.azabicyclo[3.2.1]octane-3β-carboxamido)anisole (23) from 2,3-dimethoxyaniline, 4-methylsulphonyl-2-(8'-benzyl-8'-azabicyclo[3,2,1]octane-3'β-carboxamido)anisole (24) from 2-amino-4-methylsulphonylanisole (30% yield, mp. 174°-178° C.),

EXAMPLE 1d 4-aminosulphonyl-2-(8'benzyl-8'-azabicyclo[3.2.1]octane-3'β-carboxamido)anisole (25)

2-amino-4-aminosulphonylanisole (1.9 g, 0.0094 moles) 8-benzyl-8-azabicyclo[3.2.1]octane-3-carboxylic acid hydrochloride (2.66 g, 0.0094 moles) and dicyclohexylcarbodiimide (2.3 g, 0.011 moles) in dry dimethylformamide (30 ml) were stirred together at room temperature overnight. The solvent was removed under reduced pressure, 10% aqueous sodium hydroxide was added and the aqueous solution was extracted with ethyl acetate (3×50 ml). The combined extracts were dried (MgSO₄); removal of solvent gave a brown oil. Column chromatography on alumina, eluting with ethyl acetate gave (25), which was recrystallized from ethyl acetate/light petroleum. (1.0 g, 25%) mp 162°-3° C.

EXAMPLE 2

5-Nitro-4-chloro-2-[8'-benzyl-8'-azabicyclo[3.2.1]octane-3'β-carboxamido]-anisole (26)

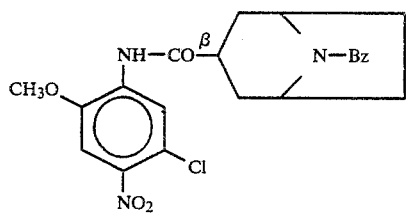

The carboxamide of Example 1 (1.4 g, 3.6 mmol) was dissolved in glacial acetic acid (13 ml) and concentrated sulphuric acid (0.9 ml) was added with stirring. The solution was cooled in an ice bath and fuming nitric acid (0.4 ml) was added dropwise. The mixture was stirred at room temperature for 2.5 hours, then poured into ice/water. It was neutralised with solid potassium carbonate, then a few ml of sodium hydroxide solution (10%) was added. The mixture was extracted with dichloromethane (4×200 ml). The combined organic extracts were dried (Na₂SO₄), filtered and evaporated to yield the desired crude nitro-carboxamide (1.8 g, 100%), as a yellow solid.

The following are prepared analogously:
5-nitro-4-chloro-2-(8'-[3",4"-dichlorobenzyl]-8'-azabicyclo[3.2.1]octane-3β'-carboxamido)anisole (27) from (2) (75% yield) mp. 148°-9° C.
5-nitro-4-chloro-2-(8'-[4"-chlorobenzyl]-8'-azabicyclo[3.2.1]octane-3β'-carboxamido]anisole (28) from (3) (100% yield) mp. 191°-2° C.
5-nitro-4-chloro-2-(8'-[4"-methylbenzyl]-8'-azabicyclo[3.2.1]octane-3β'-carboxamido)anisole (29) from (4) (100% yield)
5-nitro-4-chloro-2-(8'-[4"-methoxybenzyl]-8'-azabicyclo[3.2.1]octane-3β'-carboxamido)anisole (30) from (5) (78% yield) mp. 159°-62° C.
5-nitro-4-chloro-2-(8'-[3"-trifluoromethyl]-8'-azabicyclo[3.2.1]1 octane-3β'-carboxamido)anisole (31) from (6)
5-nitro-4-chloro-2-(8'-β-phenethyl-8'-azabicyclo[3.2.1]octane-3β'-carboxamido)anisole (32) from (7)
5-nitro-4-chloro-2-(8'-[2"-thenyl]-8'-azabicyclo[3.2.1]octane-3β'-carboxamido)anisole (33) from (8)
5-nitro-4-chloro-2-(8'-hexyl-8'-azabicyclo[3.2.1]octane-3β'-carboxamido)anisole (34) from (9) (80% yield, mp. 117°-9° C.)
5-nitro-4-chloro-2-(8'-3"-methylbutyl-8'-azabicyclo[3.2.1]octane-3β'-carboxamido)anisole (35) from (10), (77% yield) mp. 95°-6° C.
5-nitro-4-chloro-2-(8'-cyclohexyl-8'-azabicyclo[3.2.1]octane-3β'-carboxamido)anisole (36) from (11) (84% yield)
5-nitro-4-chloro-2-(8'-cyclohexylmethyl-8'-azabicyclo[3.2.1]octane-3β'-carboxamido)anisole (37) from (12)
5-nitro-4-chloro-2-(8'-benzyl-8'-azabicyclo[3.2.1]octane-2'-(+)-α-carboxamido)anisole (38) from (13), and
5-nitro-4-chloro-2-(8'-benzyl-8'-azabicyclo[3.2.1]octane-2'-(−)-α-carboxamido)anisole (39) from (14), as a racemate.
5-nitro-4-chloro-2-(8'-benzyl-8'-azabicyclo[3.2.1]octane-2'-(+)-α-acetamido)anisole (40) from (15) and
5-nitro-4-chloro-2-(8'-benzyl-8'-azabicyclo[3.2.1]octane-2'-(−)-α-acetamido)anisole (41) from (16), as a racemate.
5-nitro-4-chloro-2-(8'-benzyl-8'-azabicyclo[3.2.1]octane-3'α-acetamido)anisole (42) from (17)
5-nitro-4-chloro-2-(8'-benzyl-8'-azabicyclo[3.2.1]octane-3'β-acetamido)anisole (43) from (18)

EXAMPLE 3

5-Amino-4-chloro-2-[8'-benzyl-8'-azabicyclo-[3.2.1]octane-3'β-carboxamido]-anisole (44)

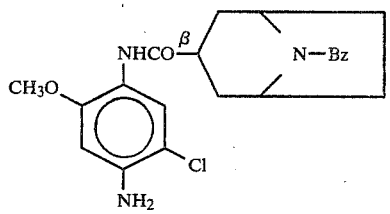

The nitro-carboxamide (0.59 g, 1.37 mmol) was dissolved in ethanol (250 ml) and 2 spatulas of W2 Raney nickel was added. This was hydrogenated at atmospheric pressure for 3 hours. The catalyst was filtered off and the filtrate was stripped to dryness. The material was chromatographed on 5% deactivated neutral alumina. Elution with ethyl acetate:petrol (1:1) gave the aminocarboxamide as a white foam (0.4 g, 73%). The analytical sample (m.p. 150°-151° C.) was recrystallised from hexane/ethyl acetate/chloroform.

The following are prepared analogously:
5-amino-4-chloro-2-(8'-[3",4"-dichlorobenzyl]-8'-azabicyclo[3.2.1]octane-3β'-carboxamido)anisole (45) from (27), (81% yield), mp 139°-140° C.;
5-amino-4-chloro-2-(8'-(4"-chlorobenzyl)-8'-azabicyclo [3.2.1]octane-3'β-carboxamido)anisole (46) from (28), (87% yield), mp 119°-121° C.;
5-amino-4-chloro-2-(8'-[4"-methylbenzyl]-8'-azabicyclo [3.2.1]octane-3'β-carboxamido)anisole (47) from (29), (84% yield), mp 132°-133° C.;
5-amino-4-chloro-2-(8'-[4"-methoxybenzyl]-8'-azabicyclo [3.2.1]octane-3'β-carboxamido)anisole (48) from (30), (61% yield), mp 90°-92° C.;

5-amino-4-chloro-2-(8'-[3''-trifluoromethylbenzyl]-8'-azabicyclo[3.2.1]octane-3'β-carboxamido)anisole (49) from (31).

5-amino-4-chloro-2-(8'-[β-phenethyl]-8'-azabicyclo[3.2.1]octane-3'β-carboxamido)anisole (50) from (32).

5-amino-4-chloro-2-(8'-[2''-thenyl]-8'-azabicyclo[3.2.1]octane-3'β-carboxamido)anisole (51) from (33).

5-amino-4-chloro-2-(8'-hexyl-8'-azabicyclo[3.2.1]octane-3'β-carboxamido)anisole (52) from (34), (65% yield), mp 96°–98° C.;

5-amino-4-chloro-2-(8'-3''-methylbutyl-8'-azabicyclo[3.2.1]octane-3'β-carboxamido)anisole (53) from (35), (68% yield), mp 139°–140° C.;

5-amino-4-chloro-2-(8'-cyclohexyl-8'-azabicyclo[3.2.1]octane-3'β-carboxamido)anisole (54) from (36) (47% yield); mp 177°–8° C.;

5-amino-4-chloro-2-(8'-cyclohexylmethyl-8'-azabicyclo[3.2.1]octane-3'β-carboxamido)anisole (55) from (37); (63% yield), mp 158°–9° C.;

5-amino-4-chloro-2-(8'-benzyl-8'-azabicyclo[3.2.1]octane-2'-(+)-α-carboxamido)anisole (56) from (38);

5-amino-4-chloro-2-(8'-benzyl-8'-azabicyclo[3.2.1]octane-2'-(−)-α-carboxamido)anisole (57) from (39), as a racemate;

5-amino-4-chloro-2-(8'-benzyl-8'-azabicyclo[3.2.1]octane-2'-(+)-α-acetamido)anisole (58) from (40), and 5-amino-4-chloro-2-(8'-benzyl-8'-azabicyclo[3.2.1]octane-2'-(−)-α-acetamido)anisole (59) from (41), as a racemate;

5-amino-4-chloro-2-(8'-benzyl-8'-azabicyclo[3.2.1]octane-3'α-acetamido)anisole (60) from (42);

5-amino-4-chloro-2-(8'-benzyl-8'-azabicyclo[3.2.1]octane-3'β-acetamido)anisole (61) from (43).

EXAMPLE 4

5-Acetamido-4-chloro-2-[8-benzyl-8-azabicyclo (3,2,1) acetone-3β-carboxamido]anisole (62)

5-amino-4-chloro-2-[8-benzyl-8-azabicyclo(3,2,1)octane 2β-carboxamido]anisole (2.3 g, 0.0057 moles) and a large excess of acetic anhydride in ethanol (50 ml) were stirred together at room temperature for 48 hours. The solvent was removed under reduced pressure and sodium carbonate solution, followed by a few drops of 10% sodium hydride solution. The aqueous solution was extracted with methylene chloride (3×100 ml) and the combined organic extracts dried (MgSO₄). Removal of solvent and recrystallisation from ethanol gave 5-acetamido-4-chloro-2-[8-benxyl-8-azabicyclo (3.2.1)-octane-3β-carboxmido]-anisole (1.35 g., 54%), m.p. 233°–5°.

The following are prepared analogously:

5-acetamido-4-chloro-2-(8'-[3'',4''-dichlorobenzyl]-8'-azabicyclo[3.2.1]octane-3'β-carboxamido)anisole (63) from (45), 5-acetamido-4-chloro-2-(8'-[4''-chlorobenzyl]-8'-azabicyclo[3.2.1]octane-3'β-carboxamido)anisole (64) from (46), 5-acetamido-4-chloro-2-(8'-[4''-methylbenzyl]-8'-azabicyclo[3.2.1]octane-3'β-carboxamido)anisole (65) from (47), 5-acetamido-4-chloro-2-(8'-[4''-methoxybenzyl]-8'-azabicyclo[3.2.1]octane-3'β-carboxamido)anisole (66) from (48), 5-acetamido-4-chloro-2-(8'-[3''-trifluoromethylbenzyl]-8'-azabicyclo[3.2.1]octane-3'β-carboxamido)anisole (67) from (49), 5-acetamido-4-chloro-2-(8'-[β-phenethyl]-8'-azabicyclo[3.2.1]octane-3β-carboxamido)anisole (68) from (50), 5-acetamido-4-chloro-2-(8'-[2''-thenyl]-8'-azabicyclo[3.2.1]octane-3β-carboxamido)anisole (69) from (51), 5-acetamido-4-chloro-2-(8'-hexyl-8'-azabicyclo[3.2.1]octane-3β-carboxamido)anisole (70) from (52), 5-acetamido-4-chloro-2-(8'-3''-methylbutyl-8'-azabicyclo[3.2.1]octane-3β-carboxamido)anisole (71) from (53), 5-acetamido-4-chloro-2-(8'-cyclohexyl-8'-azabicyclo[3.2.1]octane-3'β-carboxamido)anisole (72), from (54), 5-acetamido-4-chloro-2-(8'-cyclohexylmethyl-8'-azabicyclo[3.2.1]octane-3β-carboxamido)anisole (73) from (55), 5-acetamido-4-chloro-2-(8'-benzyl-8'-azabicyclo[3.2.1]octane-2-(+)-α-carboxamido)anisole (74) from (56), and 5-acetamido-4-chloro-2-(8'-benzyl-8'-azabicyclo[3.2.1]octane-2-(−)-α-carboxamido)anisole (75) from (57) as a racemate.

5-acetamido-4-chloro-2-(8'-benzyl-8'-azabicyclo[3.2.1]octane-2-(+)-α-acetamido)anisole (76) from (58), and 5-acetamido-4-chloro-2-(8'-benzyl-8'-azabicyclo[3.2.1]octane-2-(−)-α-acetamido)anisole (77) from (59), as a racemate, 5-acetamido-4-chloro-2-(8'-benzyl-8'-azabicyclo[3.2.1]octane-3'α-acetamido)anisole (78) from (60), 5-acetamido-4-chloro-2-(8'-benzyl-8'-azabicyclo[3.2.1]octane-3'β-acetamido)anisole (79) from (61).

The following are prepared analogously using a large excess of formic acid in place of acetic anhydride:

5-formamido-4-chloro-2-(8'-benzyl-8'-azabicyclo[3.2.1]octane-3'β-carboxamido)anisole (80) from (44), 5-formamido-4-chloro-2-(8'-[3'',4''-dichlorobenzyl]-8'-azabicyclo[3.2.1]octane-3'β-carboxamido)anisole (81) from (45).

5-formamido-4-chloro-2-(8'-[4''-chlorobenzyl]-8'-azabicyclo[3.2.1]octane-3'β-carboxamido)anisole (82) from (46), 5-formamido-4-chloro-2-(8'-[4''-methylbenzyl]-8'-azabicyclo[3.2.1]octane-3'β-carboxamido)anisole (83) from (47), 5-formamido-4-chloro-2-(8'-[4''-methoxybenzyl]-8'-azabicyclo [3.2.1]octane-3'β-carboxamido)anisole (84) from (48), 5-formamido-4-chloro-2-(8'-[3''-trifluoromethylbenzyl]-8'-azabicyclo[3.2.1]octane-3'β-carboxamido)anisole (85) from (49), 5-formamido-4-chloro-2-(8'-[β-phenethyl]-8'-azabicyclo[3.2.1]octane-3'β-carboxamido)anisole (86) from (50), 5-formamido-4-chloro-2-(8'-[2''-thenyl]-8'-azabicyclo[3.2.1] octane-3'β-carboxamido)anisole (87) from (51), 5-formamido-4-chloro-2-(8'-hexyl-8'-azabicyclo[3.2.1]octane-3'β-carboxamido)anisole (88) from (52), 5-formamido-4-chloro-2-(8'-methylbutyl-8'-azabicyclo[3.2.1]octane-3'β-carboxamido)anisole (89) from (53), 5-formamido-4-chloro-2-(8'-cyclohexyl-8'-azabicyclo[3.2.1]octane-3'β-carboxamido)anisole (90) from (54), 5-formamido-4-chloro-2-(8'-cyclohexylmethyl-8'-azabicyclo [3.2.1]octane-3'-β-carboxamido)anisole (91) from (55), 5-formamido-4-chloro-2-(8'-benzyl-8'-azabicyclo[3.2.-
1]octane-2-(+)-α-carboxamido)anisole (92) from
(56), and 5-formamido-4-chloro-2-(8'-benzyl-8'-azabicyclo[3.2.-
1]octane-2-(−)-α-carboxamido)anisole (93) from (57)
as a racemate, 5-formamido-4-chloro-2-(8'-benzyl-8'-azabicyclo[3.2.-
1]octane-2'-(+)-α-acetamido)anisole (94) from
(59), and 5-formamido-4-chloro-2-(8'-benzyl-8'-azabicyclo[3.2.-
1]octane-2'-(−)-α-acetamido)anisole (95) from
(59), as a racemate, 5-formamido-4-chloro-2-(8'-benzyl-8'-azabicyclo[3.2.-
1]octane-3'α-acetomido)anisole (96) from (60), 5-formamido-4-chloro-2-(8'-benzyl-8'-azabicyclo[3.2.-
1]octane-3'β-acetomido)anisole (97) from (61).

Pharmacological Data (i) Inhibition of Apomorphine Induced Climbing in the
Mouse The compound prepared in Example 3 was tested for
inhibition of apomorphine induced climbing behaviour
in the mouse. This is indicative of dopamine receptor
blockade in the central nervous system.

The test is based on that described by Protais, P.,
Constantin, J. and Schwartz, J. C. (1976), Psychopharmacology, 50, 1–6.

Apomorphine 1 mg/kg s.c. induces mice to climb the
wall of a wire cage (inverted food hopper—11×7.5×18
cm high). Mice acclimatised in their home cages in
groups of 5 are placed under the hoppers immediately
after the injection of apomorphine 1 mg/kg s.c. At 10,20
and 30 minutes after injection climbing behaviour is
scored. The mice are observed for 30 seconds and
scored according to the position they spend the majority of time in, score 0—four paws on floor of cage; score
1—fore paws only on walls; score 2—all paws on wall
of cage. The scores at all 3 times and for each mouse are
summed and mice drug treated orally 30 min. prior to
apomorphine compared to mice receiving apomorphine
only. A saline only treated group is also included and
any score, generally 5% of maximum taken into account.

The results are shown in the following Table.

TABLE

| Compound No. | Dose mg/kg | Activity % Inhibition |
|---|---|---|
| 44 | 1 | 100 |
|  | (ED$_{50}$ 0.05) |  |
| 45 | 10 | 100 |
| 48 | 10 | 100 |
| 46 | 10 | 100 |
| 47 | 10 | 100 |
| 53 | 10 | 56 |
| 62 | 2 | 95 |
| 55 | 50 | 100 |
| 20 | 10 | 100 |
| 21 | 2 | 60 |

(ii) Gastric Motility Testing in the Rat

The compounds were tested for ability to reverse the
inhibition effect of 6,7-ADTN on gastric motility recorded by an open tipped catheter in the conscious
chronic gastric fistula rat. Administration of 1 mg/kg
s.c. of 6,7-ADTN reduced basal gastric motor activity
and this was reversed by the administration of 1 mg/kg
s.c. of the compound (24) or 5 mg/kg s.c. of the compound (25) administered 10 minutes after the 6,7-ADTN. Control injections did not reverse the inhibition. For subcutaneous testing the compounds were
dissolved in water by the addition of tartaric acid (½
mole per mole of compound).

(iii) Anti-emetic Activity in the Dog

Compounds were administered subcutaneously 30
minutes, or per os 2 hr, prior to administration of a
standard dose of apomorphine HCl (0.1 mg/kg subcutaneously) and the vomiting response compared to that
obtained when the same animals were dosed with apomorphine HCl and vehicle only. The dose that totally
inhibited the vomiting response was determined in some
instances, the active dose in others.

(24) completely inhibited the response at 0.1 mg/kg
s.c.

(25) was active at 2 mg/kg p.o.

Toxicity

No toxic effects were observed in the tests reported
above at the test dosages.

We claim:

1. A compound of the formula (III) or a pharmaceutically acceptable salt thereof:

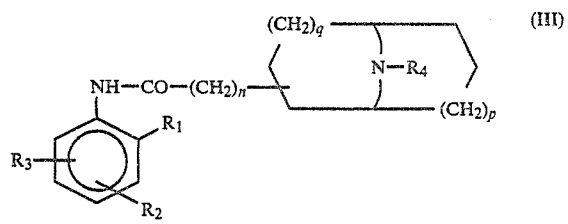

wherein:

$R_1$ is a $C_{1-6}$ alkoxy or $C_{1-6}$ alkylthio group;

$R_2$ is hydrogen, halogen, $CF_3$, $C_{1-7}$ alkanoyl; $C_{1-7}$ alkanoylamino or amino, aminocarbonyl optionally
substituted by one or two $C_{1-6}$ alkoxy, $C_{1-6}$ alkylthio,
hydroxy or nitro; or $R_1$ and $R_2$ taken together are
methylenedioxy or ethylenedioxy $R_3$ is hydrogen, halogen, $CF_3$, $C_{1-7}$ alkanoyl $C_{1-7}$ alkanoylamino or amino, aminocarbonyl or aminosulphonyl optionally substituted by one or two $C_{1-6}$ alkyl
groups, $C_{1-6}$ alkylthio, hydroxy or nitro;

$R_4$ is $C_{1-7}$ alkyl or a group —$(CH_2)_sR_6$ where s is 0 to 2
and $R_6$ is a $C_{3-8}$ cycloalkyl group, or a group —$(CH_2)_sR_7$ where t is 1 or 2 and $R_7$ is a phenyl
group optionally substituted by one or two substituents selected from $C_{1-6}$ alkyl, $C_{1-4}$ alkoxy, trifluoromethyl and halogen, or a thienyl group; and n, p and q are independently 0 to 2.

2. A compound according to claim 1, wherein:

$R_1$ is $C_{1-6}$ alkoxy;

$R_2$ and $R_3$ are the same or different and are hydrogen,
halogen, trifluoromethyl, $C_{2-7}$ alkanoyl, $C_{1-7}$ alkanoylamino, or amino, aminocarbonyl or aminosulphonyl optionally substituted by one or two $C_{1-6}$ alkyl
groups; $C_{1-6}$ alkylsulphonyl or nitro provided that
only $R_3$ may contain a sulphonyl moiety; or $R_1$ and $R_2$ taken together are methylenedioxy or ethylenedioxy, in which case $R_3$ may be any one of the
groups given for $R_2$ and $R_3$ above;

$R_4$ is $C_{1-7}$ alkyl or a group —$(CH_2)_sR_6$ where s is 0 to 2
and $R_6$ is a $C_{3-8}$ cycloalkyl group, or a group
—$(CH_2)_tR_7$ where t is 1 or 2 and $R_7$ is a phenyl group
optionally substituted by one or two substituents selected from $C_{1-6}$ alkyl, $C_{1-6}$ alkoxy, trifluoromethyl and halogen; and n, p and q are independently 0 to 2.

3. A compound according to claim 1 of formula (VI):

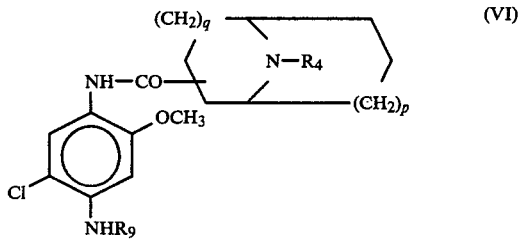

wherein $R_9$ is hydrogen or $C_{1-4}$ alkanoylamino and $R_4$, p and q are as defined in claim 2.

4. A compound according to claim 3 of formula (VII):

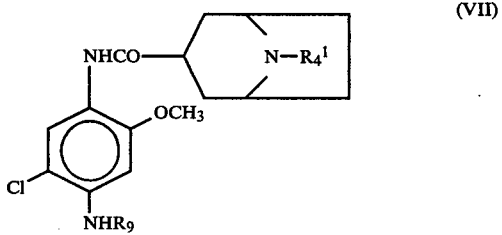

wherein $R^1_4$ is $C_{5-7}$ alkyl and $R_9$ is as defined in claim 3.

5. A compound according to claim 4, wherein the NHCO moiety is in the β-orientation to the nortropane ring.

6. 5-amino-4-chloro-2-(8'-3-methylbutyl-8'-azabicyclo[3.2.1]octane-3'β-carboxamido)anisole;
5-acetamido-4-chloro-2-(8'-3-methylbutyl-8'-azabicyclo[3.2.1]octane-3'β-carboxamido)anisole; or
5-formamido-4-chloro-2-(8'-3-methylbutyl-8'-azabicyclo[3.2.1]octane-3'β-carboxamido)anisole; or a pharmaceutically acceptable salt thereof.

7. A compound according to claim 3 of formula (VIII):

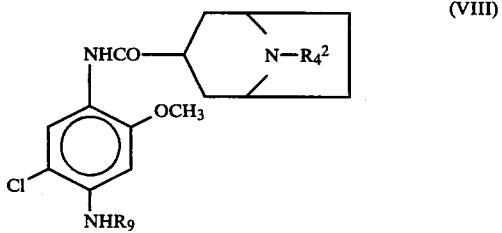

wherein $R^2_4$ is a group —$(CH_2)_t R^1_7$ wherein t is 1 or 2 and $R^1_7$ is optionally substituted phenyl as defined in formula (III); cyclohexylmethyl; or 2-thienylmethyl; and $R_9$ is as defined in claim 3.

8. A compound according to claim 7, wherein NHCO moiety is in the β-orientation to the nortropane ring.

9. 4-chloro-2-(8'-benzyl-8'-azabicyclo[3.2.1]octane-3'β-carboxamido)anisole,
5-nitro-4-chloro-2-(8'-benzyl-8'-azabicyclo[3.2.1]octane-3'β-carboxamido)anisole,
5-amino-4-chloro-2-(8'-benzyl-8'-azabicyclo[3.2.1]octane-3'β-carboxamido)anisole,
5-acetamido-4-chloro-2-(8'-benzyl-8'-azabicyclo[3.2.1]octane-3'β-carboxamido)anisole,
5-formamido-4-chloro-2-(8'-benzyl-8'-azabicyclo[3.2.1]octane-3'β-carboxamido)anisole,
4-chloro-2-(8'-[4"-chlorobenzyl]-8'-azabicyclo(3.2.1]octane-3'β-carboxamido)anisole
5-nitro-4-chloro-2-(8'-[4"-chlorobenzyl]-8'-azabicyclo[3.2.1]octane-3'β-carboxamido)anisole,
5-amino-4-chloro-2-(8'-[4"-chlorobenzyl]-8'-azabicyclo[3.2.1]octane-3'β-carboxamido)anisole,
5-acetamido-4-chloro-2-(8'-[4"-chlorobenzyl]-8'-azabicyclo[3.2.1]octane-3'β-carboxamido)anisole,
5-formamido-4-chloro-2-(8'-[4"-chlorobenzyl]-8'-azabicyclo[3.2.1]octane-3'β-carboxamido)anisole,
4-chloro-2-(8'-[4"-methylbenzyl]-8'-azabicyclo[3.2.1]octane-3'β-carboxamido)anisole,
5-nitro-4-chloro-2-(8'-[4"-methylbenzyl]-8'-azabicyclo[3.2.1]octane-3'β-carboxamido)anisole,
5-amino-4-chloro-2-(8'-[4"-methylbenzyl)-8'-azabicyclo[3.2.1]octane-3'β-carboxamido)anisole,
5-acetamido-4-chloro-2-(8'-[4"-methylbenzyl]-8'-azabicyclo[3.2.1]octane-3'β-carboxamido)anisole,
5-formamido-4-chloro-2-(8'-[4"methylbenzyl]-8'-azabicyclo[3.2.1]octane-3'β-carboxamido)anisole,
4-chloro-2-(8'-[4"-methoxybenzyl]-8'-azabicyclo[3.2.1]octane-3'β-carboxamido)anisole,
5-nitro-4-chloro-2-(8'-[4"-methoxybenzyl]-8'-azabicyclo[3.2.1]octane-3'β-carboxamido)anisole,
5-amino-4-chloro-2-(8'-[4"-methoxybenzyl]-8'-azabicyclo[3.2.1]octane-3'β-carboxamido)anisole,
5-acetamido-4-chloro-2-(8'-[4"-methoxybenzyl]-8'-azabicyclo[3.2.1]octane-3'β-carboxamido)anisole,
5-formamido-4-chloro-2-(8'-[4"-methoxybenzyl]-8'-azabicyclo[3.2.1]octane-3'β-carboxamido)anisole,
4-chloro-2-(8'-[3",4"-dichlorobenzyl]-8'-azabicyclo[3.2.1]octane-3'β-carboxamido)anisole,
5-nitro-4-chloro-2-(8'-[3",4"-dichlorobenzyl]-8'-azabicyclo[3.2.1]octane-3'β-carboxamido)anisole,
5-amino-4-chloro-2-(8'-[3",4"-dichlorobenzyl]-8'-azabicyclo[3.2.1]octane-3'β-carboxamido)anisole,
5-acetamido-4-chloro-2-(8'-[3",4"-dichlorobenzyl]-8'-azabicyclo[3.2.1]octane-3'β-carboxamido)anisole,
5-formamido-4-chloro-2-(8'-[3",4"-dichlorobenzyl]-8'-azabicyclo[3.2.1]octane-3'β-carboxamido)anisole,
4-chloro-2-(8'-cyclohexylmethyl-8'-azabicyclo[3.2.1]octane-3'β-carboxamido)anisole,
5-nitro-4-chloro-2-(8'-cyclohexylmethyl-8'-azabicyclo[3.2.1]octane-3'β-carboxamido)anisole,
5-amino-4-chloro-2-(8'-cyclohexylmethyl-8'-azabicyclo[3.2.1]octane-3'β-carboxamido)anisole,
5-acetamido-4-chloro-2-(8'-cyclohexylmethyl-8'-azabicyclo[3.2.1]octane-3'β-carboxamido)anisole,
5-formamido-4-chloro-2-(8'-cyclohexylmethyl-8'-azabicyclo[3.2.1]octane-3'β-carboxamido)anisole,
or a pharmaceutically acceptable salt thereof.

10. A compound according to claim 1 of formula (XI):

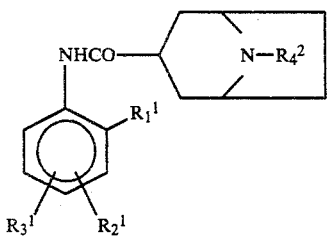

wherein:

$R^1_1$ is $C_{1-6}$alkoxy;

$R^1_2$ and $R^1_3$ are the same or different and are hydrogen, aminosulphonyl optionally substituted by one or two $C_{1-6}$ alkyl groups, $C_{1-6}$ alkylsulphonyl, $C_{1-6}$ alkylsulphinyl or $C_{1-6}$ alkoxy provided that only $R^1_3$ may contain a sulphonyl or sulphinyl moiety; or $R^1_1$ and $R^1_2$ taken together are methylenedioxy or ethylenedioxy; and $R^2_4$ is $-(CH_2)_tR^1_7$ wherein t is 1 or 2 and $R^1_7$ is optionally substituted phenyl, cyclohexylmethyl or 2-thienylmethyl.

11. A compound according to claim 10 of formula (XII):

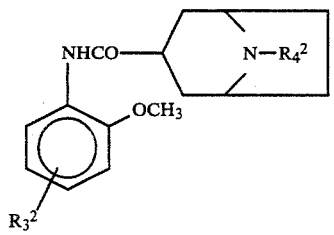

wherein $R^2_3$ is aminosulphonyl optionally substituted by one or two $C_{1-6}$ alkyl groups, $C_{1-6}$ alkylsulphonyl or $C_{1-6}$ alkylsulphinyl and $R^2_4$ is as defined in claim 7.

12. A compound according to claim 11, wherein the NHCO moiety is in the $\beta$-orientation to the nortropane ring.

13. 4-aminosulphonyl-2-(8'-benzyl-8'azabicyclo[3.2.1]octane-3'$\beta$-carboxamido)anisole or 4-methylsulphonyl-2-(8'-benzyl-8'-azabicyclo[3.2.1]octane-3'-$\beta$-carboxamido)anisole, or a pharmaceutically acceptable salt thereof.

14. A compound according to claim 10 of formula (XIII)

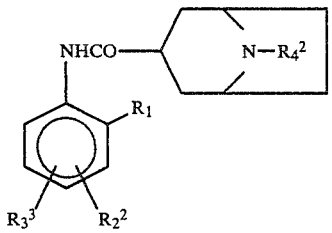

wherein:

$R^1_1$ and $R^2_4$ are as defined in claim 10;

$R^2_2$ and $R^3_3$ are the same or different and are $C_{1-6}$ alkoxy; or $R^1_1$ and $R^2_2$ taken together are methlenedioxy or ethylenedioxy, in which case $R^3_3$ is any one of the groups given above for $R^2_2$ and $R^3_3$ subject to the proviso of claim 10.

15. A compound according to claim 14, wherein the NHCO moiety is in the $\beta$-orientation to the nortropane ring.

16. 3-methoxy-4-(8'-benzyl-8'-azabicyclo[3.2.1]octane-3'$\beta$-carboxamido)anisole,
4-methoxy-2-(8'-benzyl-8'-azabicyclo[3.2.1]octane-3'$\beta$-carboxamido)anisole,
2,3-ethylenedioxy-(8'-benzyl-8'-azabicyclo[3.2.1]octane-3'$\beta$-carboxanilide.

17. A pharmaceutical composition for the treatment or prophylaxis of emesis, which comprises an antiemetic amount of a compound of the formula (III) as defined in claim 1, or a pharmaceutically acceptable salt thereof together with a pharmaceutically acceptable carrier.

* * * * *